(12) United States Patent
Miyatani

(10) Patent No.: US 10,018,535 B2
(45) Date of Patent: Jul. 10, 2018

(54) THIN-SLICE MANUFACTURING DEVICE AND THIN-SLICE MANUFACTURING METHOD

(71) Applicant: SAKURA FINETEK JAPAN CO., LTD., Tokyo (JP)

(72) Inventor: Tatsuya Miyatani, Tokyo (JP)

(73) Assignee: SAKURA FINETEK JAPAN CO., LTD, Tokyo (JP)

( * ) Notice: Subject to any disclaimer, the term of this patent is extended or adjusted under 35 U.S.C. 154(b) by 110 days.

(21) Appl. No.: 14/897,944

(22) PCT Filed: Jun. 26, 2014

(86) PCT No.: PCT/JP2014/067064
§ 371 (c)(1),
(2) Date: Dec. 11, 2015

(87) PCT Pub. No.: WO2015/002070
PCT Pub. Date: Jan. 8, 2015

(65) Prior Publication Data
US 2016/0139006 A1 May 19, 2016

(30) Foreign Application Priority Data

Jul. 3, 2013 (JP) .................................. 2013-140012

(51) Int. Cl.
*G01N 1/06* (2006.01)
*G01N 1/36* (2006.01)

(52) U.S. Cl.
CPC ................. *G01N 1/06* (2013.01); *G01N 1/36* (2013.01); *G01N 2001/068* (2013.01); *Y10T 83/0538* (2015.04)

(58) Field of Classification Search
CPC ......... G01N 1/06; G01N 2001/061–2001/068; G01C 2009/066

(Continued)

(56) References Cited

U.S. PATENT DOCUMENTS 5,729,337 A * 3/1998 Tanaka ..................... G01C 9/06
356/139.1
5,933,393 A * 8/1999 Kitajima .............. G01C 15/004
33/276

(Continued)

FOREIGN PATENT DOCUMENTS

EP 2813833 12/2014
JP 2002-539424 11/2002

(Continued)

OTHER PUBLICATIONS

International Search Report from corresponding PCT Application No. PCT/JP2014/067064 dated Oct. 7, 2014. English translation attached.

(Continued)

*Primary Examiner* — Kenneth E Peterson
(74) *Attorney, Agent, or Firm* — Grossman, Tucker, Perreault & Pfleger, PLLC

(57) ABSTRACT

A thin-slice manufacturing device is a thin-slice manufacturing device for cutting an embedding block in which a biological sample is embedded by paraffin using a cutting blade relatively moved with respect to the embedding block along a virtual plane to cut out thin slices, the thin-slice manufacturing device includes a vertical illumination part configured to radiate light to the embedding block, and an inclination estimation part configured to detect a boundary line between a cutting surface cut along the virtual plane and a non-cutting surface based on reflection of light generated by the light radiated to the embedding block by the vertical illumination part, and estimate inclination information showing information related to inclination of the embedding block based on the detected boundary line.

12 Claims, 12 Drawing Sheets

(58) Field of Classification Search
USPC .................................. 83/915.5; 356/139.1
See application file for complete search history.

(56) References Cited

U.S. PATENT DOCUMENTS

| | | | | |
|---|---|---|---|---|
| 6,046,799 | A * | 4/2000 | Lysen | G01B 11/272 356/139.1 |
| 6,594,006 | B1 * | 7/2003 | Muehlhoff | G05B 19/402 356/139.03 |
| 6,634,268 | B1 | 10/2003 | Guenther et al. | |
| 6,778,266 | B2 * | 8/2004 | Hu | G01B 11/26 356/138 |
| 7,830,501 | B2 * | 11/2010 | Kludas | G01C 11/06 356/139.03 |
| 7,859,687 | B2 * | 12/2010 | Mitsutake | G01B 11/0608 250/235 |
| 8,064,055 | B2 * | 11/2011 | Liphardt | G01B 11/272 356/139.1 |
| 8,514,382 | B2 * | 8/2013 | Bach | G01B 11/272 250/559.3 |
| 9,513,119 | B2 * | 12/2016 | Goldstein | G01C 11/06 |
| 2004/0189983 | A1 * | 9/2004 | Takahashi | G01B 11/26 356/139.1 |
| 2006/0164630 | A1 * | 7/2006 | Hofbauer | G01B 11/26 356/141.1 |
| 2007/0199418 | A1 | 8/2007 | Ito | |
| 2008/0072723 | A1 * | 3/2008 | Nakajima | B26D 5/02 83/102 |
| 2009/0231573 | A1 * | 9/2009 | Urashima | G01B 11/26 356/139.1 |
| 2010/0118133 | A1 | 5/2010 | Walter et al. | |
| 2011/0134416 | A1 * | 6/2011 | Ke | G01B 11/306 356/123 |
| 2012/0092653 | A1 * | 4/2012 | Liphardt | G01B 11/272 356/139.1 |
| 2013/0335558 | A1 * | 12/2013 | Choiniere | G01B 11/26 348/135 |
| 2014/0053421 | A1 * | 2/2014 | Fan | G01C 9/20 33/366.16 |

FOREIGN PATENT DOCUMENTS

| | | |
|---|---|---|
| JP | 2007-212276 | 8/2007 |
| JP | 2007-212387 | 8/2007 |
| JP | 2007-218616 | 8/2007 |
| JP | 2008-020293 | 1/2008 |
| JP | 2008-76251 | 4/2008 |
| JP | 4840765 | 12/2011 |
| WO | 2012/147730 | 11/2012 |

OTHER PUBLICATIONS

Extended Search Report from corresponding EPO Application No. 14819757.7 dated Feb. 2, 2017.

\* cited by examiner

THIN-SLICE MANUFACTURING DEVICE AND THIN-SLICE MANUFACTURING METHOD

TECHNICAL FIELD

The present invention relates to a thin-slice manufacturing device and a thin-slice manufacturing method.

Priority is claimed on Japanese Patent Application No. 2013-140012, filed Jul. 3, 2013, the contents of which are incorporated herein by reference.

BACKGROUND ART

As a method of inspecting or observing a biological sample extracted from a human body, an experimental animal, or the like, a method of manufacturing a thin slice from an embedding block is known in which a biological sample is embedded by an embedding agent, performing a staining process with respect to the thin slice, and observing the biological sample.

In recent years, a thin-slice manufacturing device capable of automatically performing an operation of manufacturing the thin slice has begun to be provided. Such a thin-slice manufacturing device manufactures a thin slice by relatively moving a cutting blade and an embedding block in a predetermined feed direction and cutting the embedding block with a thickness of several μm (for example, 3 μm to 5 μm).

Incidentally, when the above-mentioned thin slice is manufactured, the embedding block should be cut in a specific cross section such that a tissue (a biological sample) to be inspected or observed appears on a surface thereof. Conventionally, while the embedded tissue is embedded such that a cross section to be sliced and observed is parallel to an end surface of a block, the cross section is not completely parallel to the end surface. For this reason, in a slicing operation by a microtome, an operation called surface shaping is performed. The surface shaping is an operation in which an operator repeats the adjustment of the inclination of the embedding block and slicing the embedding block until the cross section of the tissue to be observed appears on a surface thereof when observing the embedded tissue. A thickness of the embedding block cut upon the surface shaping is relatively thick, and the cutting is referred to as rough cutting.

The embedding block processed by the above-mentioned thin-slice manufacturing device is constituted by two types of an embedding block upon termination of the above-mentioned surface shaping and an embedding block that is still uncut. The above-mentioned thin-slice manufacturing device requires surface matching when the embedding block upon termination of the surface shaping is processed. The surface matching is a work of measuring the inclination of the end surface of the embedding block to adjust the inclination such that the end surface becomes parallel to the cutting surface of the thin slice manufacturing apparatus.

As a technology of performing the surface matching of the cutting surface, for example, a technology disclosed in Patent Document 1 is known. In the technology disclosed in Patent Document 1, positions of three corners of the embedding block are detected using a sensor, and the surface matching of the cutting surface is performed based on the positions of three corners.

As a technology of automatically performing the surface shaping of the uncut block, there is a technology disclosed in Patent Document 2. In the technology disclosed in Patent Document 2, the block end surface is imaged for every cut, and the surface shaping is performed based on a variation in an area of the exposed tissue.

PRIOR ART DOCUMENTS

Patent Documents

Patent Document 1: Japanese Unexamined Patent Application Publication (Translation of PCT Application) No. 2002-539424

Patent Document 2: Japanese Patent No. 4840765

SUMMARY OF INVENTION

Problems to be Solved by the Invention

However, in Patent Document 1, for example, at least three positions should be measured using the sensor. In addition, in Patent Document 1, for example, when the cutting surface of the embedding block does not coincide with a cross section of a biological sample appropriate for inspection or observation, the surface shaping may not be appropriately performed. For this reason, in the technology disclosed in Patent Document 1, the thin slice having an appropriate cross section may not be manufactured.

In addition, in Patent Document 2, for example, when the cross section is inclined with respect to the cutting surface, the appropriate surface shaping cannot be performed.

The present invention is directed to provide a thin-slice manufacturing device and a thin-slice manufacturing method capable of manufacturing a thin slice of an appropriate cross section, i.e., performing surface shaping even when a cross section of an embedded tissue is inclined with respect to a cutting surface while performing surface matching of the cutting surface without the necessity of inclination detection of an embedding block by a sensor.

Means for Solving the Problems

A thin-slice manufacturing device according to an aspect of the present invention employs the following configurations.

(1) A thin-slice manufacturing device according to an aspect of the present invention is a thin-slice manufacturing device for cutting an embedding block in which a sample is embedded by an embedding agent by using a cutting blade relatively moved with respect to the embedding block along a virtual plane to cut out thin slices, and the thin-slice manufacturing device includes: a radiation part configured to radiate light to the embedding block; and an estimation part configured to detect a boundary line between a cutting surface and a non-cutting surface formed by cutting the embedding block along the virtual plane based on reflection of light generated by the light radiated to the embedding block from the radiation part, and configured to estimate inclination information regarding inclination of the embedding block based on the detected boundary line.

(2) In the above-mentioned aspect (1), the inclination information may include a direction of the inclination of the embedding block and a degree of inclination of the embedding block, and the estimation part may estimate the direction of the inclination based on a normal vector of the boundary line, and simultaneously, estimate the degree of inclination based on a movement amount of the boundary line and a predetermined amount when the virtual plane is moved by the predetermined amount in a direction perpendicular to the virtual plane in order to cut the embedding block.

(3) In the above-mentioned aspect (2), the movement amount of the boundary line may be a movement amount in a direction of the normal vector.

(4) In the above-mentioned aspect (2) or (3), the normal vector of the boundary line may be an average normal vector, and the estimation part may estimate the direction of the inclination based on the average normal vector.

(5) In the above-mentioned aspect (2) or (3), the normal vector of the boundary line may be a vector having a largest magnitude among a vector in a normal direction of the boundary line having the movement amount of the boundary line as a magnitude, and the estimation part may estimate the direction of the inclination based on the vector having the largest magnitude.

(6) In the above-mentioned aspect (2) or (3), the radiation part may switch and radiate vertical illumination light and diffuse light to the embedding block, the estimation part may detect the boundary line based on reflection of the vertical illumination light, the normal vector of the boundary line may be a vector in a normal direction of the boundary line in which a magnitude thereof is set as a length until to the outline of the sample obtained based on radiation of the diffuse light, and the estimation part may estimate the direction of the inclination based on the vector in the normal direction of the boundary line in which a magnitude thereof is set as the length until to the outline of the sample.

(7) In the above-mentioned aspect (6), the estimation part may estimate the direction of the inclination based on the vector having the largest magnitude among the vector in the normal direction of the boundary line in which a magnitude thereof is set as the length until to the outline of the sample.

(8) In the above-mentioned aspect (6), the estimation part may estimate the direction of the inclination based on the average vector in the normal direction of the boundary line in which a magnitude thereof is set as the length until to the outline of the sample as the magnitude.

(9) In any one of the above-mentioned aspects (1) to (8), a compensation part configured to compensate the inclination of the embedding block so that the predetermined cross section of the embedding block and the virtual plane are parallel to each other based on the inclination information estimated by the estimation part may be provided.

(10) In the above-mentioned aspect (9), the boundary line may include a boundary line between a cutting surface and a non-cutting surface of the embedding agent, the predetermined cross section of the embedding block may include a roughly cut surface showing a predetermined cutting surface on which a rough cutting, which previously cuts a surface of the predetermined cross section of the embedding block to the predetermined cutting surface, is performed, and the compensation part may compensate the inclination of the embedding block so that the roughly cut surface and the virtual plane are parallel to each other based on the inclination information.

(11) In the above-mentioned aspect (9) or (10), the boundary line may include a boundary line between a cutting surface and a non-cutting surface of the sample, the predetermined cross section of the embedding block may include a predetermined cross section of the sample, and the compensation part may compensate the inclination of the embedding block so that the predetermined cross section of the sample and the virtual plane are parallel to each other based on the inclination information.

(12) In the above-mentioned aspect (10), the boundary line may include a boundary line between a cutting surface and a non-cutting surface of the sample, the predetermined cross section of the embedding block may include a predetermined cross section of the sample, and the compensation part may compensate the inclination of the embedding block so that the roughly cut surface and the virtual plane are parallel to each other based on the inclination information when the rough cutting is performed on the embedding block, and compensate the inclination of the embedding block so that the predetermined cross section of the sample and the virtual plane are parallel to each other based on the inclination information when the rough cutting is performed on the embedding block.

(13) In any one of the above-mentioned aspects (9) to (12), the thin-slice manufacturing device may include an inclination angle change part configured to change an inclination of a support section configured to fix the embedding block; and an imaging part configured to image an image of the embedding block by reflection of the light in a state in which the light is radiated from the radiation part, wherein the estimation part may detect the boundary line based on the image imaged by the imaging part and estimate the inclination information based on the detected boundary line, and the compensation part may change the inclination of the support section using the inclination angle change part based on the inclination information.

(14) A thin-slice manufacturing method according to another aspect of the present invention is a thin-slice manufacturing method of cutting an embedding block in which a sample is embedded by an embedding agent by using a cutting blade relatively moving with respect to the embedding block along a virtual plane in order to cut out thin slices, and the thin-slice manufacturing method includes: a radiation step of radiating light to the embedding block by a radiation part; and an estimation step of detecting a boundary line between a cutting surface cut along the virtual plane and a non-cutting surface based on reflection of light generated by the light radiated to the embedding block in the radiation step by an estimation part, and estimating inclination information regarding inclination of the embedding block based on the detected boundary line.

Advantage of Invention

According to the aspects of the present invention, the thin slice having the appropriate cross section can be manufactured while the surface matching of the cutting surface can be performed without the necessity of inclination detection of the embedding block by the sensor.

DESCRIPTION OF EMBODIMENTS

Hereinafter, a thin-slice manufacturing device according to an embodiment of the present invention will be described with reference to the accompanying drawings.

First Embodiment

Figure 1:
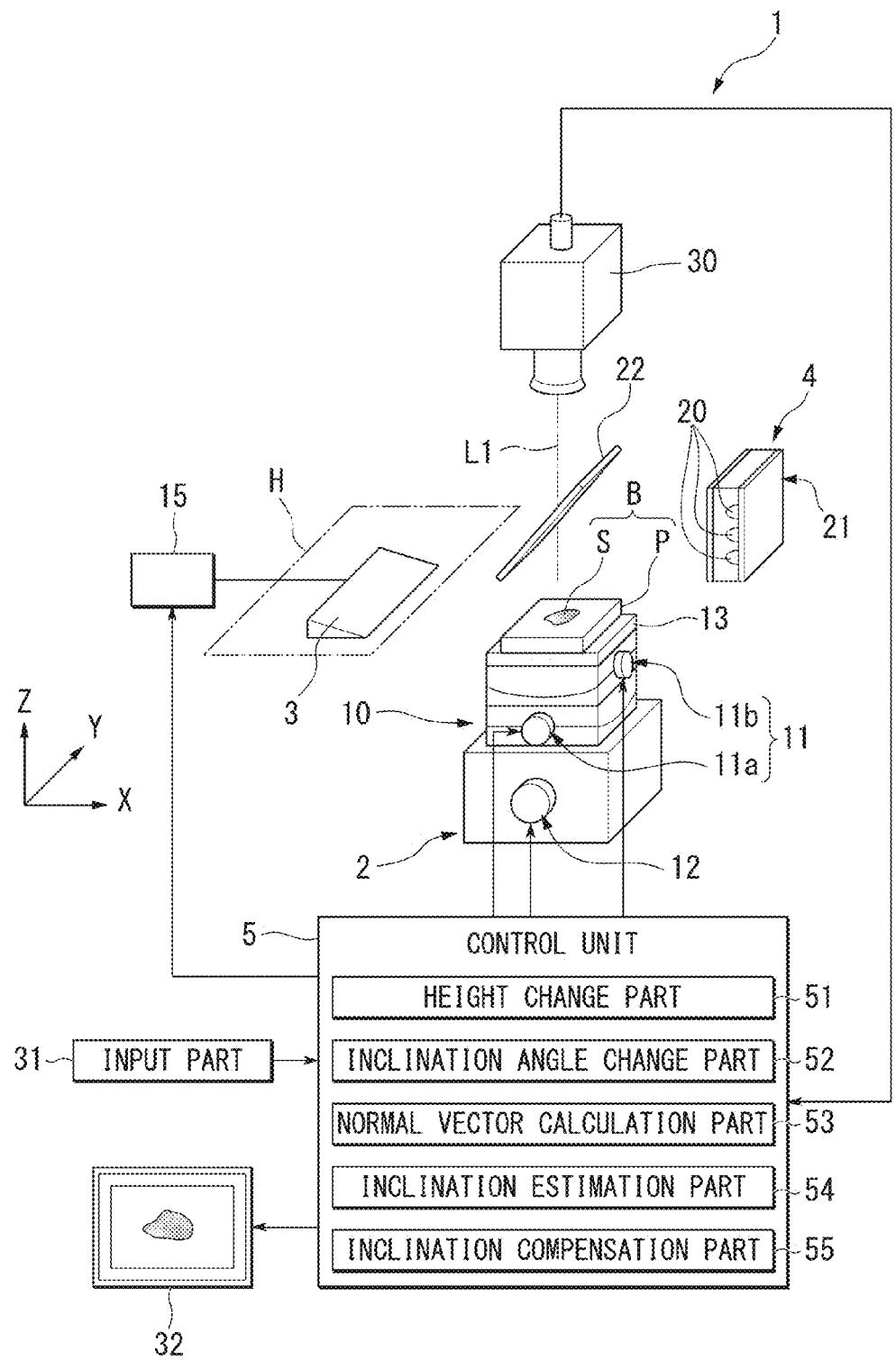
FIG. 1 is a block diagram showing an example of a thin-slice manufacturing device according to a first embodiment.

FIG. 1 is a block diagram showing an example of a thin-slice manufacturing device 1 according to a first embodiment.

Figure 2:
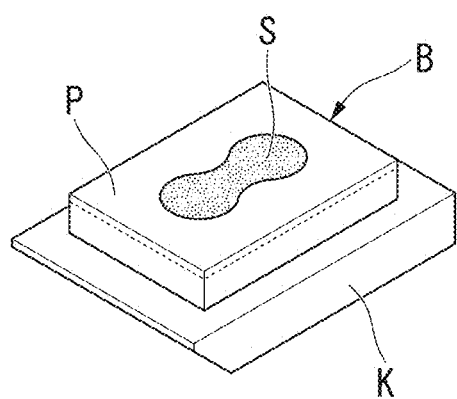
FIG. 2 is a perspective view showing an example of an embedding block according to the present embodiment.

In addition, FIG. 2 is a perspective view showing an example of an embedding block B according to the present embodiment.

The thin-slice manufacturing device 1 is a device for cutting the embedding block B shown in FIG. 2 using a cutting blade 3 to cut out thin slices. The cutting blade 3 relatively moves with respect to the embedding block B along a virtual plane H. For example, the thin-slice manufacturing device 1 manufactures thin slices (for example, thin slices having a thickness of 3 μm to 5 μm) by cutting the embedding block B after rough cutting and surface shaping of the embedding block B in which a biological sample S is embedded in paraffin P is performed. Here, for example, the "surface shaping" is performed to expose a cross section of a tissue of the biological sample S to be sliced to a surface of the embedding block B. In addition, the "rough cutting" is performed to cut the embedding block B in thick pieces (roughly) to perform the surface shaping.

Further, in the present embodiment, the case in which the thin-slice manufacturing device 1 cuts out thin slices with respect to the embedding block B at which some degree of surface shaping has been previously performed by a device such as a microtome or the like will be described. In addition, the thin-slice manufacturing device 1 will be described as previously measuring the highest position (a height in a Z-axis direction) of the embedding block B using a sensor (not shown) (for example, an optical sensor, an electrical sensor, or the like). Further, as a measurement method of the highest position of the embedding block B, the method is not limited to the method using the sensor but another known measurement method may be applied.

In FIG. 2, the embedding block B has a rectangular shape when seen in a plan view in which a periphery thereof is further fixed in a block shape by the paraffin P (an embedding agent) after moisture in the biological sample S fixed by formalin is substituted with the paraffin. Accordingly, the biological sample S is embedded in the paraffin P. In addition, as the biological sample S (a sample), for example, a tissue of an internal organ or the like extracted from a human body, an experimental animal, or the like, is provided, and appropriately selected in the fields of medicine, pharmaceuticals, food, biology, or the like.

In addition, the embedding block B is fixed onto a cassette K as shown in FIG. 2.

The cassette K is formed of a resin or the like having a chemical resistance in a box shape, and functions as a fixing frame configured to fix the embedding block B. One side surface of the cassette K becomes an inclined surface that is directed downward. ID data (not shown) including a manufacturing date of the embedding block B, various data of the biological sample S, and so on, are recorded in the inclined surface. For this reason, in the embedding block B, quality management of the embedding block B can be performed by reading the ID data of the cassette K.

In FIG. 1, the thin-slice manufacturing device 1 includes a base section 2, the cutting blade 3, a vertical illumination part 4, a control unit 5, an imaging part 30, an input part 31 and a display part 32.

The base section 2 has a support frame 10 having a block holder 13 (a support section) on which the embedding block B is placed, a swing mechanism part 11, and a movement mechanism part 12 configured to move the support frame 10 in a Z-axis direction perpendicular to the virtual plane H. In addition, the base section 2 is disposed on an optical axis L1 of the vertical illumination part 4.

The block holder 13 is a support section disposed at a distal end of the support frame 10 and configured to fix the embedding block B and the cassette K to the support frame 10.

The swing mechanism part 11 rotates the support frame 10 and the block holder 13 about two axes, i.e., an X-axis and a Y-axis perpendicular to each other on the virtual plane H. In addition, the swing mechanism part 11 is constituted by a Y-axis swing mechanism part 11a configured to rotate the support frame 10 about the Y-axis and an X-axis swing mechanism part 11b configured to rotate the support frame 10 about the X-axis, and operated based on an instruction from the control unit 5.

The movement mechanism part 12 is configured to move the swing mechanism part 11 and the support frame 10 in the Z-axis direction, and operated based on an instruction from the control unit 5 like the swing mechanism part 11.

The cutting blade 3 relatively moves with respect to the embedding block B along the virtual plane H to cut the embedding block B. In the present embodiment, as an example, the cutting blade 3 is connected to a cutting blade movement mechanism part 15 that moves in the X-axis direction. Accordingly, the cutting blade 3 is configured to move along the virtual plane H.

The cutting blade movement mechanism part 15 is configured to receive an instruction from the control unit 5 to be operated, and moving speed (cutting speed), cutting timing, and so on, are controlled.

The vertical illumination part 4 (a radiation part) radiates parallel light to the embedding block B. For example, the vertical illumination part 4 has the optical axis L1 perpendicular to the virtual plane H and directed toward a surface of the embedding block B (the cutting surface) on the support frame 10. The vertical illumination part 4 has a surface light source 21 having a plurality of LEDs 20 disposed in a planar shape, an optical system (not shown) configured to change the light radiated from the surface light source 21 into parallel light, and a half mirror 22.

The half mirror 22 reflects the parallel light from the surface light source 21 toward the surface of the embedding block B on the support frame 10 and allows the reflected light from the embedding block B to pass therethrough.

Further, the light source may be configured to allow the light from a point light source, other than the surface light source 21, to pass through a pinhole and a collimating lens to change the light into parallel light.

In the present embodiment, the light radiated from the light source (the surface light source 21) is reflected by the half mirror 22 to obtain the optical axis L1 directed toward the surface of the embedding block B. However, the light source may be disposed to be directly facing the surface of the embedding block B to obtain the optical axis L1 without installing the half mirror 22.

The imaging part 30 includes an imaging element (not shown), and is set such that an imaging axis coincides with the optical axis L1. In addition, the imaging part 30 images the embedding block B from a vertical upper side under illumination light of the vertical illumination part 4. That is, the imaging part 30 images an image of the embedding block B by reflection of the parallel light in a state in which the light from the vertical illumination part 4 is radiated. Image data imaged by the imaging part 30 is temporarily stored in an image storage (not shown) to be output to the control unit 5 (to be described below).

Further, hereinafter, the image (or the image data) of the embedding block B imaged under the illumination of the vertical illumination part 4 (under the coaxial vertical illumination) is referred to as a vertical illumination image (or vertical illumination image data).

The input part 31 is an input device such as a keyboard, a mouse, a joystick, or the like, configured to perform various types of manipulations of the thin-slice manufacturing device 1, and configured to input information such as various settings or the like to the thin-slice manufacturing device 1. The input part 31 outputs the input manipulation information, setting information and input information to the control unit 5.

The display part 32 is a monitor such as a liquid crystal display or the like, and displays an image imaged by the imaging part 30, an image obtained by processing the image, various screens of the thin-slice manufacturing device 1, a setting screen, an information input screen, and so on.

The control unit 5 (a controller) is, for example, a control device having a central processing unit (CPU, not shown), and performs various types of controls of the thin-slice manufacturing device 1.

For example, the control unit 5 performs a surface matching process of disposing the embedding block B such that the cutting surface of the embedding block B or the biological sample S is parallel to the virtual plane H of the cutting blade 3. Further, in the present embodiment, the case in which rough cutting of the embedding block B has been previously performed and the control unit 5 performs the surface matching process (or the surface shaping process) so that a roughly cut surface of the embedding block B is parallel to the virtual plane H of the cutting blade 3 will be described. Here, for example, the "surface matching" is performed to adjust the inclination and cut the embedding block B such that the end surface of the embedding block B is parallel to the cutting surface.

The control unit 5 includes a height change part 51, an inclination angle change part 52, a normal vector calculation part 53, an inclination estimation part 54 and an inclination compensation part 55.

The height change part 51 controls the movement mechanism part 12 of the base section 2 to adjust a height of the embedding block B.

The inclination angle change part 52 changes the inclination of the block holder 13 configured to fix the embedding block B and the inclination of the support frame 10. That is, the inclination angle change part 52 controls the swing mechanism part 11 (the Y-axis swing mechanism part 11a and the X-axis swing mechanism part 11b) to change the inclination of the block holder 13 and the inclination of the support frame 10.

The inclination estimation part 54 (the estimation part) detects a boundary line between the cutting surface cut along the virtual plane H and the non-cutting surface (the uncut surface) based on reflection of the light generated by the parallel light radiated to the embedding block B by the vertical illumination part 4, and estimates inclination information showing information related to inclination of the embedding block B based on the detected boundary line. Here, the inclination information includes, for example, a direction of the inclination, and a degree of inclination (an inclination angle).

Further, in the present embodiment, the inclination information is, for example, the direction of inclination of the roughly cut surface of the embedding block B, and the degree of the inclination (an inclination angle). The inclination estimation part 54 estimates the direction of the inclination of the roughly cut surface of the embedding block B, and the degree of the inclination (the inclination angle).

The above-mentioned cutting surface cut along the virtual plane H is a cross section newly cut by the cutting blade 3 with respect to the roughly cut surface. In addition, the non-cutting surface (the uncut surface) is a cross section that is still not cut by the device, and the roughly cut surface is included in the non-cutting surface (the uncut surface).

Specifically, the inclination estimation part 54 images the image in a state in which the parallel light is radiated to the embedding block B by the vertical illumination part 4 (for example, the image shown in FIGS. 3 and 4) by the imaging part 30. The inclination estimation part 54 detects the boundary line between the cutting surface and the non-cutting surface (the uncut surface) based on the image imaged by the imaging part 30, and estimates the inclination information (the direction of the inclination and the inclination angle) based on the detected boundary line.

Figure 3:
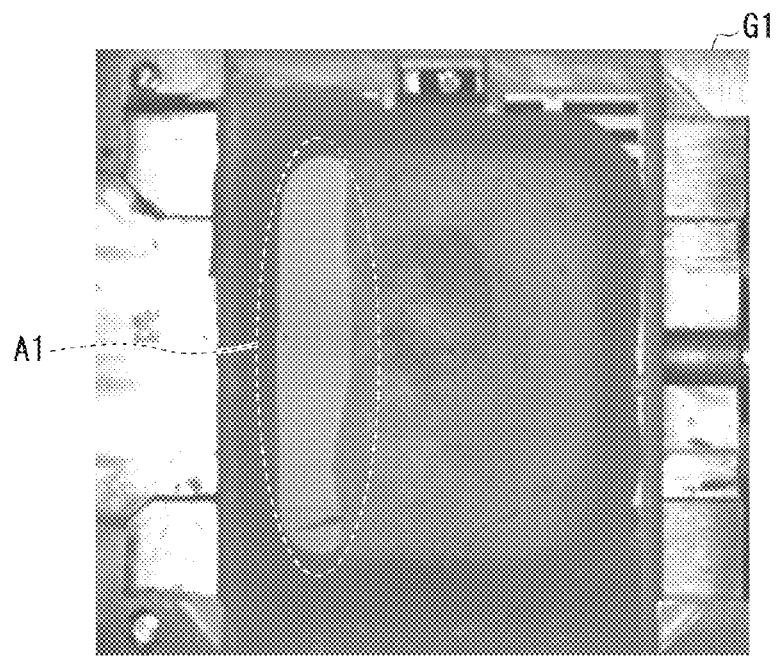
FIG. 3 is a first view showing an example of a vertical illumination image of the embedding block according to the present embodiment.

Since the vertical illumination light is radiated from the vertical illumination part 4 to the embedding block B, for example, as shown in FIG. 3, a variation in brightness occurs in the image (the vertical illumination image) imaged by the imaging part 30 between the cutting surface and the non-cutting surface.

FIG. 3 is a first view showing an example of the vertical illumination image of the embedding block B according to the present embodiment.

In FIG. 3, an image G1 is a vertical illumination image of the embedding block B, and an area (a range) A1 having high brightness shows a cutting surface. Further, in comparison with the area A1 in the image G1, a portion having lower brightness corresponds to a non-cutting surface (an uncut surface) in the roughly cut surface.

The inclination estimation part 54 detects the boundary line between the cutting surface and the non-cutting surface based on a variation in brightness of the vertical illumination image obtained by acquiring the image from the imaging part 30, and causes the normal vector calculation part 53 (to be described below) to calculate a normal vector with respect to the boundary line.

The inclination estimation part 54 estimates the direction of the normal vector calculated by the normal vector calculation part 53 as the direction of the inclination.

In addition, the inclination estimation part 54 acquires the vertical illumination image from the imaging part 30 again by relatively moving the virtual plane H by a predetermined amount (for example, a thickness ΔTs) in a direction perpendicular to the virtual plane H to be cut by the cutting blade 3 again. Here, for example, the imaging part 30 images the vertical illumination image such as an image G2 of FIG. 4. Further, in the present embodiment, the predetermined amount (for example, the thickness ΔTs) is referred to as a delivery amount in a height direction (a Z-axis direction).

Figure 4:
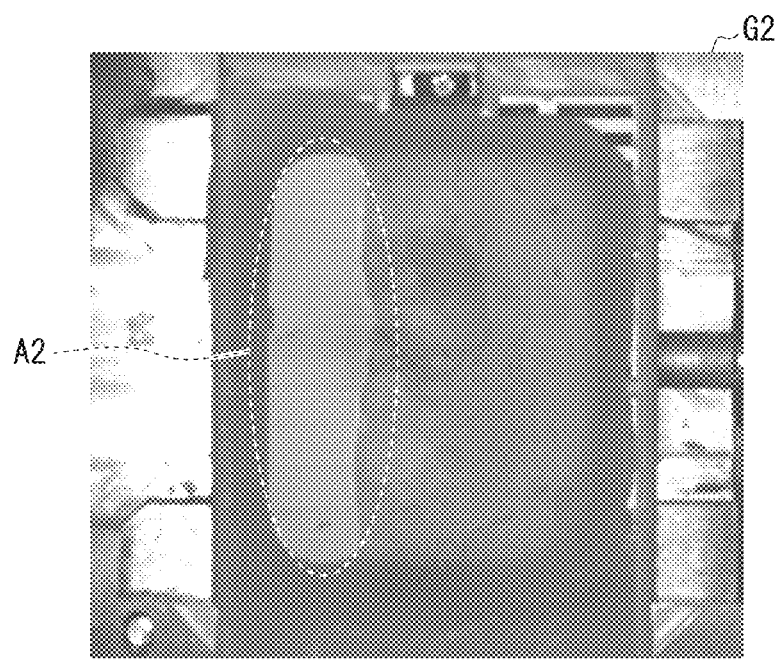
FIG. 4 is a second view showing an example of the vertical illumination image of the embedding block according to the present embodiment.

FIG. 4 is a second view showing an example of a vertical illumination image of the embedding block B according to the present embodiment.

In FIG. 4, the image G2 is the vertical illumination image of the embedding block B cut by a predetermined amount from a state of the image G1 shown in FIG. 3, and an area (a range) A2 having high brightness shows a cutting surface. Further, in the image G2, the area A2 of the cutting surface is shown as being wider than the area A1 of the image G1.

The inclination estimation part 54 detects the boundary line between the cutting surface and the non-cutting surface and calculates the movement amount of the boundary line based on a variation in the brightness of the vertical illumination image acquired from the imaging part 30. Here, the movement amount of the boundary line is a movement amount in the direction of the normal vector. The inclination estimation part 54 calculates the inclination angle based on the calculated movement amount of the boundary line and the above-mentioned predetermined amount (the thickness ΔTs). Further, the inclination estimation part 54 calculates the inclination angle of the roughly cut surface using a trigonometric function (to be described below).

In this way, for example, the inclination estimation part 54 estimates the direction of the inclination based on the normal vector of the boundary line, and simultaneously, estimates the degree of inclination (the inclination angle) based on the movement amount of the boundary line when the virtual plane H is moved by the predetermined amount (the thickness ΔTs) in the direction perpendicular to the virtual plane H in order to perform the cutting, and based on the predetermined amount.

The normal vector calculation part 53 calculates the normal vector of the boundary line based on the boundary line between the cutting surface and the non-cutting surface detected by the inclination estimation part 54. For example, the normal vector calculation part 53 approximates the boundary line to a straight line and calculates the normal vector of the approximate straight line when the boundary line is a curve. The normal vector calculation part 53 outputs the calculated normal vector to the inclination estimation part 54.

Further, the normal vector calculation part 53 may calculate an average normal vector as the normal vector. For example, when the boundary line is a curve, the normal vector calculation part 53 can calculate one direction by calculating the average normal vector.

In addition, the normal vector calculation part 53 may generate a straight line (for example, straight lines such as a boundary line BL1 of FIG. 6 and a boundary line BL2 of FIG. 7) passing through both ends of the boundary line (contact points between ends of the embedding block B and the boundary line), and may calculate the normal vector with respect to the generated straight line as the normal vector of the boundary line.

The inclination compensation part 55 (the compensation part) compensates the inclination of the embedding block B so that a predetermined cross section of the embedding block B is parallel to the virtual plane H based on the inclination information estimated by the inclination estimation part 54. For example, the boundary line between the cutting surface and the non-cutting surface of the paraffin P is included in the above-mentioned boundary line, and the roughly cut surface showing the predetermined cutting surface having a surface previously roughly cut by a predetermined cutting surface is included in a predetermined cross section of the embedding block B. The inclination compensation part 55 compensates the inclination of the embedding block B so that the roughly cut surface and the virtual plane H are parallel to each other based on the inclination information (the direction of the inclination and the inclination angle of the roughly cut surface).

Specifically, the inclination compensation part 55 changes the inclinations of the block holder 13 and the support frame 10 with respect to the inclination angle change part 52. That is, the inclination angle change part 52 controls the swing mechanism part 11 (the Y-axis swing mechanism part 11a and the X-axis swing mechanism part 11b) and changes the inclination of the block holder 13 and the inclination of the support frame 10 so that the roughly cut surface and the virtual plane H are parallel to each other.

Next, the operation of the thin-slice manufacturing device 1 according to the present embodiment will be described with reference to the accompanying drawings. In the present embodiment, the operation when the surface matching process is performed with respect to the roughly cut surface of the embedding block B will be described.

Here, first, processing of estimating the direction of the inclination of the roughly cut surface by the inclination estimation part 54 will be described.

<Estimation Process of Direction of Inclination in Roughly Cut Surface>

Figure 5:
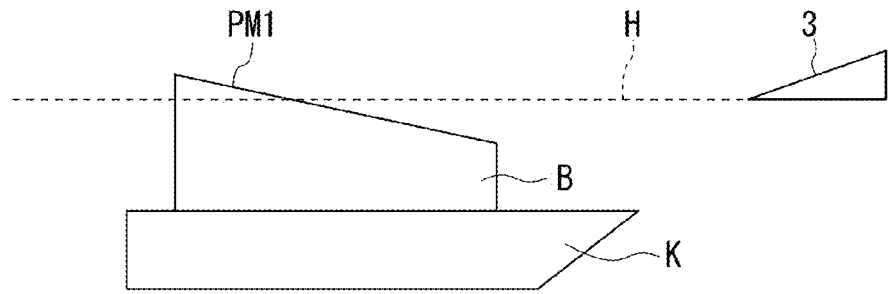
FIG. 5 is a cross-sectional view showing an example in which the embedding block upon termination of rough cutting according to the first embodiment is cut.

FIG. 5 is a cross-sectional view showing an example of cutting the embedding block B in which the rough cutting has been performed according to the first embodiment.

In FIG. 5, the embedding block B is fixed onto the cassette K while a roughly cut surface PM1 is disposed upward. FIG. 5 shows a state in which the cutting blade 3 is relatively moved with respect to the embedding block B along the virtual plane H to cut the roughly cut surface PM1 of the embedding block B. In this way, after the cutting blade 3 cuts the embedding block B, when the vertical illumination part 4 radiates the vertical illumination, the embedding block B is observed from the imaging part 30 as shown in FIG. 6.

Figure 6:
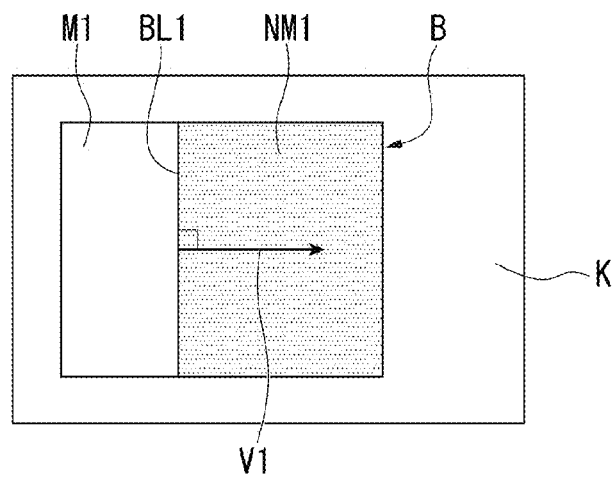
FIG. 6 is a first view showing a detection example of an inclination direction of the embedding block according to the first embodiment.

FIG. 6 is a first view showing a detection example of an inclination direction of the embedding block B according to the present embodiment.

In FIG. 6, a cutting surface M1 of the embedding block B cut along the virtual plane H shown in FIG. 5 is observed brighter, and a non-cutting surface NM1 of the embedding block B is observed darker. The inclination estimation part 54 acquires the image data of the embedding block B in this state imaged by the imaging part 30 from the imaging part 30, and detects the boundary line BL1 between the cutting surface M1 and the non-cutting surface NM1 based on the variation in brightness of the acquired vertical illumination image. Further, herein, the boundary line BL1 between the cutting surface M1 and the non-cutting surface NM1 is the boundary line between the cutting surface and the non-cutting surface of the paraffin P.

In addition, the normal vector calculation part 53 calculates a normal vector V1 of the boundary line BL1 to output the normal vector V1 to the inclination estimation part 54. The inclination estimation part 54 estimates a direction of inclination of the roughly cut surface PM1 in the embedding block B based on the normal vector V1 calculated by the normal vector calculation part 53.

Specifically, the inclination estimation part 54 estimates (determines) a direction of the normal vector V1 calculated by the normal vector calculation part 53 as a direction of the inclination of the roughly cut surface PM1.

Figure 7:
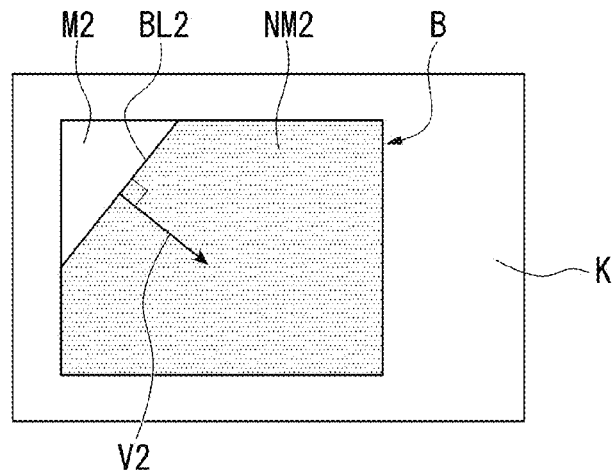
FIG. 7 is a second view showing a detection example of an inclination direction of the embedding block according to the first embodiment.

In addition, FIG. 7 is a second view showing a detection example in the inclination direction different from FIG. 6 of the embedding block B according to the present embodiment.

In FIG. 7, a cutting surface M2 of the embedding block B in which the roughly cut surface PM1 has been cut is observed brighter, and a non-cutting surface NM2 of the embedding block B is observed darker. Further, in FIG. 7, the direction of the inclination of the roughly cut surface PM1 is an inclined direction of the embedding block B, and the inclination estimation part 54 detects the boundary line BL2 between the cutting surface M2 and the non-cutting surface NM2. In addition, the inclination estimation part 54 estimates (determines) a direction of a normal vector V2 of the boundary line BL2 calculated by the normal vector calculation part 53 as a direction of the inclination of the roughly cut surface PM1.

In this way, the inclination estimation part 54 detects a boundary line between the cutting surface and the non-cutting surface of the paraffin P serving as the boundary line between the cutting surface and the non-cutting surface of the roughly cut surface, and estimates the direction of the inclination of the roughly cut surface as the inclination direction of the embedding block B based on the normal vector of the detected boundary line.

Next, a process of estimating the degree of inclination (the inclination angle) of the roughly cut surface by the inclination estimation part 54 will be described with reference to FIG. 8.

<Estimation Process of Degree of Inclination (Inclination Angle) of Roughly Cut Surface>

Figure 8:
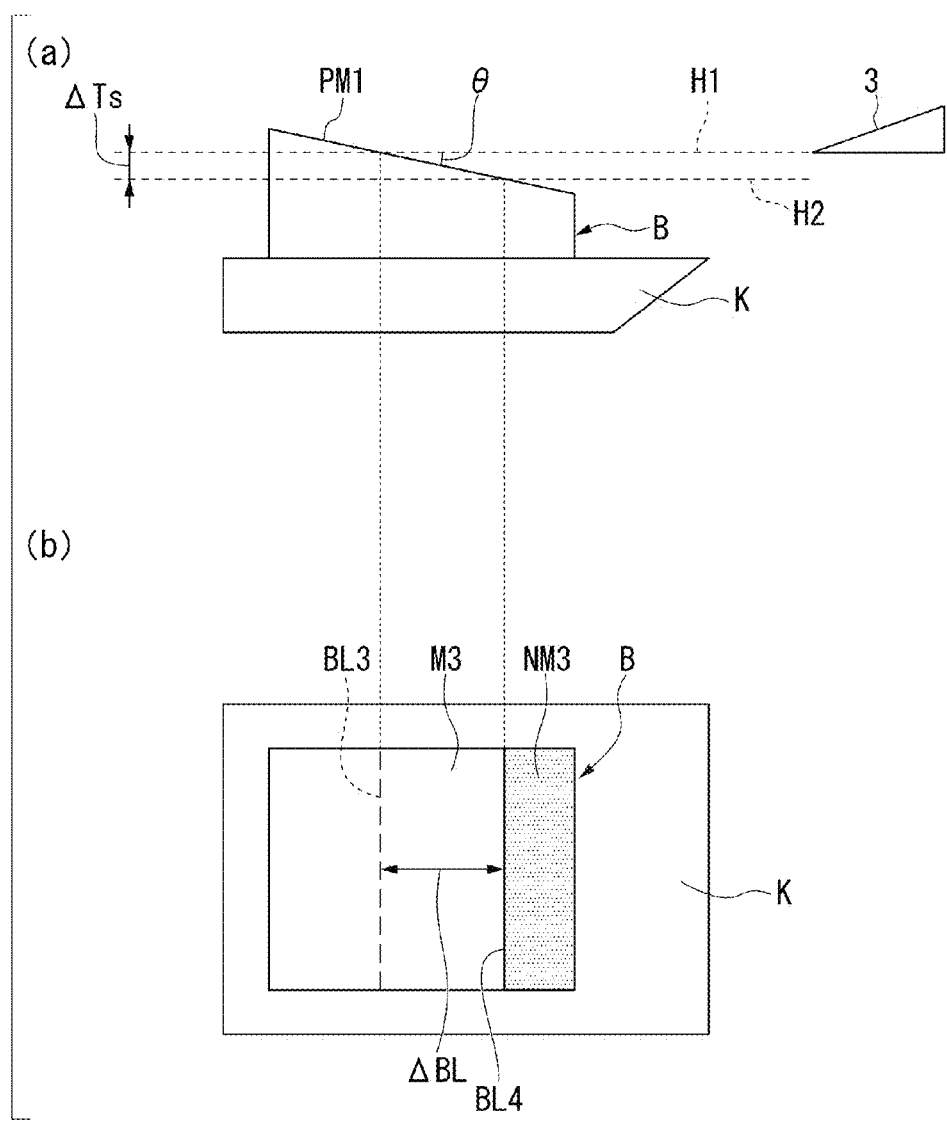
FIG. 8 is a view showing a detection example of an inclination angle of the embedding block according to the first embodiment.

FIG. 8 is a view showing a detection example of an inclination angle of the embedding block B according to the present embodiment.

FIG. 8(a) is a cross-sectional view of the embedding block B fixed onto the cassette K while the roughly cut surface PM1 is directed upward like FIG. 5. In addition, FIG. 8(a) shows a state that, after the cutting blade 3 cuts the roughly cut surface PM1 of the embedding block B along the virtual plane H1, the cutting blade 3 is delivered in the Z direction by the predetermined amount (the thickness $\Delta Ts$), and the cutting blade 3 cuts the roughly cut surface PM1 of the embedding block B along the virtual plane H2.

In addition, FIG. 8(b) shows a state of the embedding block B observed by the imaging part 30, as shown in FIG. 8(a), when the vertical illumination part 4 radiates the vertical illumination after the cutting blade 3 cuts the embedding block B along the virtual plane H2.

In FIG. 8, a boundary line BL3 shows the boundary line (the boundary line upon the last cutting) between the cutting surface and the non-cutting surface of the paraffin P after the cutting blade 3 cuts the roughly cut surface PM1 of the embedding block B along the virtual plane H1. In addition, a boundary line BL4 shows a boundary line (a boundary line upon this cutting) between a cutting surface M3 and a non-cutting surface NM3 of the paraffin P after the cutting blade 3 cuts the roughly cut surface PM1 of the embedding block B along the virtual plane H2.

The inclination estimation part 54 acquires the vertical illumination image imaged by the imaging part 30 after cutting by the cutting blade 3 along the virtual plane H1 and the vertical illumination image after cutting along the virtual plane H2 by the cutting blade 3 from the imaging part 30. The inclination estimation part 54 detects the boundary lines BL3 and BL4 between the cutting surface and the non-cutting surface and calculates a movement amount $\Delta BL$ of the boundary line based on a variation in brightness of the vertical illumination image acquired from the imaging part 30. Here, the movement amount $\Delta BL$ of the boundary line is a movement amount in a direction of a normal vector. The inclination estimation part 54 calculates an inclination angle $\theta$ using the following equation (1) based on the calculated movement amount $\Delta BL$ of the boundary line and the predetermined amount (the thickness $\Delta Ts$).

$$\tan \theta = (\text{delivery amount of embedding block } B(\text{thickness } \Delta Ts))/\text{movement amount } \Delta BL \text{ of boundary line})$$

$$\text{Inclination angle } \theta = \tan^{-1}(\text{thickness } \Delta Ts/\text{movement amount } \Delta BL \text{ of boundary line}) \quad \text{Equation (1)}$$

In this way, for example, the inclination estimation part 54 estimates the degree of inclination (the inclination angle $\theta$) based on the movement amount $\Delta BL$ of the boundary line when virtual planes (H1 and H2) are moved by the predetermined amount (the thickness $\Delta Ts$) in a direction perpendicular to the virtual planes in order to perform the cutting, and based on the predetermined amount (the thickness $\Delta Ts$).

Next, the thin slice manufacturing process operation of the thin-slice manufacturing device 1 according to the present embodiment will be described with reference to FIG. 9.

<Operation Procedure of Thin Slice Manufacturing Process>

Figure 9:
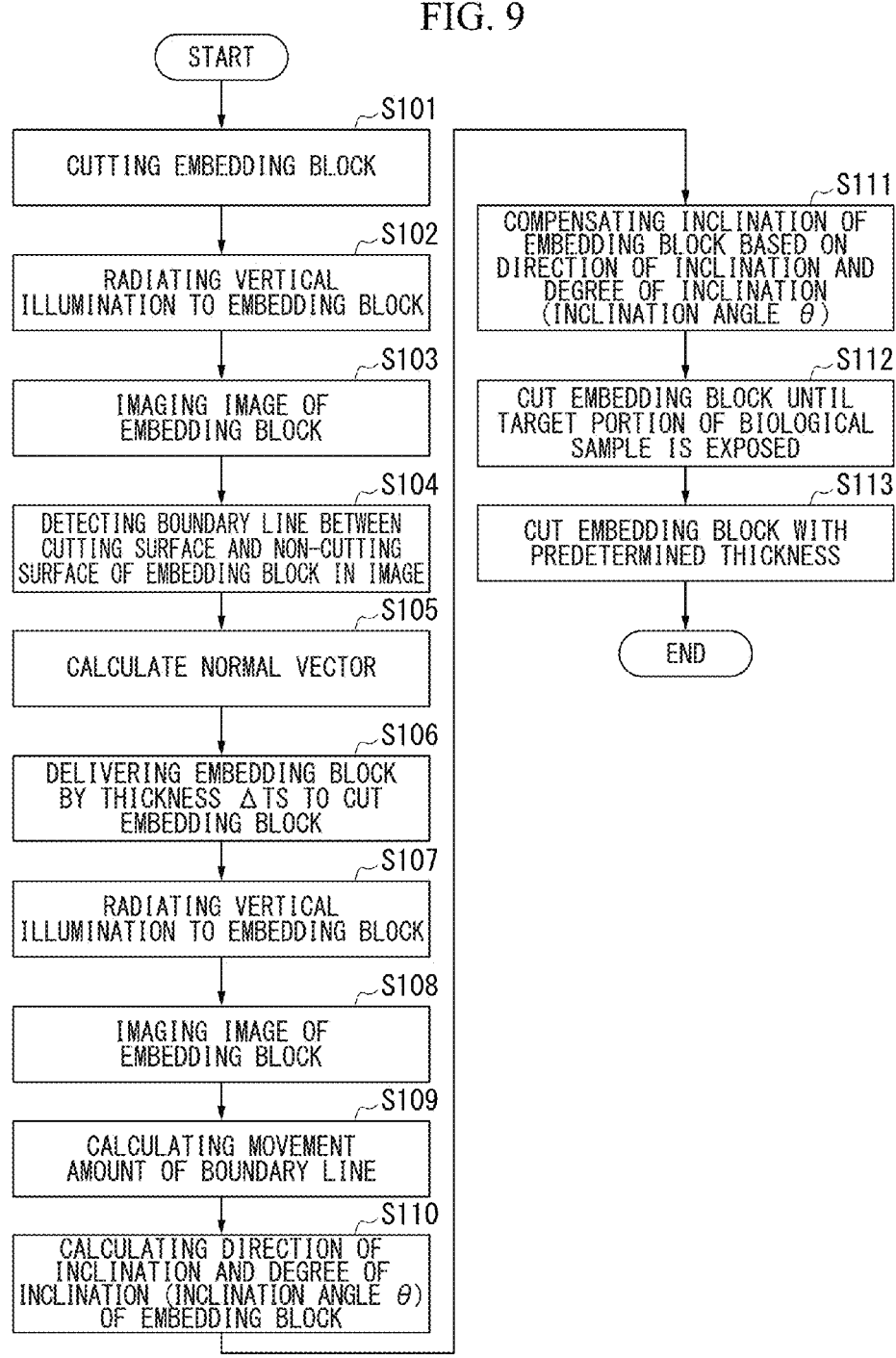
FIG. 9 is a flowchart showing an example of an operation of the thin-slice manufacturing device according to the first embodiment.

FIG. 9 is a flowchart showing an example of an operation of the thin-slice manufacturing device 1 according to the present embodiment.

In FIG. 9, the embedding block B is set on the support frame 10 of the base section 2 via the block holder 13. The thin-slice manufacturing device 1 starts the thin slice manufacturing process in a state in which the swing mechanism part 11 is in an initial state (X=0, Y=0) and the support frame 10 is horizontally disposed. Further, the embedding block B is in a state in which the embedding block B is previously roughly cut somewhat level. In addition, the thin-slice manufacturing device 1 is configured to previously measure the highest position (the height in the Z-axis direction) of the embedding block B by a sensor (not shown).

First, the thin-slice manufacturing device 1 cuts the embedding block B (step S101). That is, the height change part 51 of the control unit 5 controls the movement mechanism part 12 of the base section 2 and adjusts the movement mechanism part 12 to a predetermined height of the embedding block B. Then, the control unit 5 causes the cutting blade movement mechanism part 15 to move the cutting blade 3 along the virtual plane H. Accordingly, the thin-slice manufacturing device 1 performs cutting of the embedding block B.

Next, the vertical illumination part 4 radiates the vertical illumination to the embedding block B (step S102).

That is, the vertical illumination part 4 radiates the parallel light generated by the surface light source 21 in the direction perpendicular to the virtual plane H to the cut embedding block B.

Next, the imaging part 30 images an image of the embedding block B (step S103). That is, the inclination estimation part 54 of the control unit 5 causes the imaging part 30 to image the vertical illumination image.

Next, the inclination estimation part 54 of the control unit 5 detects the boundary line between the cutting surface and the non-cutting surface of the embedding block B in the image (step S104). The inclination estimation part 54 acquires the vertical illumination image from the imaging part 30, and detects the boundary line between the cutting surface and the non-cutting surface based on the brightness of the acquired vertical illumination image.

Next, the normal vector calculation part 53 of the control unit 5 calculates the normal vector of the boundary line (step S105). That is, the normal vector calculation part 53 calculates the normal vector of the boundary line based on the boundary line between the cutting surface and the non-cutting surface detected by the inclination estimation part 54.

Next, the thin-slice manufacturing device 1 delivers the embedding block B by the thickness $\Delta Ts$ and cuts the embedding block B (step S106). That is, the height change part 51 of the control unit 5 controls the movement mechanism part 12 of the base section 2, and moves the embedding block B by the thickness $\Delta Ts$ to be delivered in the Z-axis direction. Then, the control unit 5 causes the cutting blade movement mechanism part 15 to move the cutting blade 3 along the virtual plane H. Accordingly, the thin-slice manufacturing device 1 delivers the embedding block B by the thickness $\Delta Ts$ and cuts the embedding block B. For example, the inclination estimation part 54 instructs the movement mechanism part 12 and simultaneously instructs the cutting blade movement mechanism part 15 via the height change part 51 to perform such control processing.

Next, the vertical illumination part 4 radiates the vertical illumination to the embedding block B (step S107).

That is, the vertical illumination part 4 radiates the parallel light generated by the surface light source 21 in the direction perpendicular to the virtual plane H to the cut embedding block B.

Next, the imaging part 30 images an image of the embedding block B (step S108). That is, the inclination estimation part 54 of the control unit 5 causes the imaging part 30 to image the vertical illumination image.

Next, the inclination estimation part 54 calculates the movement amount of the boundary line (step S109). Specifically, the inclination estimation part 54 acquires the vertical illumination image imaged in step S108 from the imaging part 30, and detects the boundary line between the cutting surface and the non-cutting surface based on the brightness of the acquired vertical illumination image. The inclination estimation part 54 calculates the movement amount $\Delta BL$ to the boundary line detected at this time from the boundary line detected previously. Further, the inclination estimation part 54 calculates the movement amount $\Delta BL$ of the boundary line by the movement amount in the direction of the normal vector.

Next, the inclination estimation part 54 calculates the direction of the inclination of the embedding block B and the degree of inclination (the inclination angle θ) (step S110). Specifically, the inclination estimation part 54 calculates the direction of the inclination of the embedding block B based on the normal vector calculated by the normal vector calculation part 53 in step S105. Further, in the present embodiment, the inclination estimation part 54 calculates the direction of the inclination of the roughly cut surface as the direction of the inclination of the embedding block B. In addition, the inclination estimation part 54 calculates the degree of inclination (the inclination angle θ) using the above-mentioned equation (1) based on the movement amount $\Delta BL$ of the boundary line calculated in step S109 and the above-mentioned thickness $\Delta Ts$. Further, in the present embodiment, the inclination estimation part 54 calculates the degree of inclination (the inclination angle θ) of the roughly cut surface as the degree of inclination of the embedding block B.

In this way, for example, the inclination estimation part 54 estimates the direction of the inclination based on the normal vector of the boundary line, and simultaneously, estimates the degree of inclination (the inclination angle θ) based on the movement amount $\Delta BL$ of the boundary line when the virtual plane H is moved by the predetermined amount (the thickness $\Delta Ts$) in the direction perpendicular to the virtual plane H and cut and the predetermined amount (the thickness $\Delta Ts$).

Next, the inclination compensation part 55 of the control unit 5 compensates the inclination of the embedding block B based on the direction of the inclination and the degree of inclination (the inclination angle θ) (step S111). Specifically, the inclination compensation part 55 compensates the inclination of the embedding block B so that the roughly cut surface and the virtual plane H are parallel to each other based on the inclination information (the direction of the inclination and the inclination angle of the roughly cut surface). The inclination compensation part 55 changes the inclination of the block holder 13 and the support frame 10 with respect to the inclination angle change part 52. That is, the inclination angle change part 52 controls the swing mechanism part 11 (the Y-axis swing mechanism part 11a and the X-axis swing mechanism part 11b), and changes the inclination of the block holder 13 and the inclination of the support frame 10 so that the roughly cut surface and the virtual plane H are parallel to each other.

Next, the control unit 5 cuts the embedding block B until a target portion of the biological sample S is exposed (step S112). That is, the control unit 5 causes the height change part 51 to repeat the process of delivering the embedding block B by a predetermined thickness and cutting the embedding block B by the cutting blade movement mechanism part 15 with the cutting blade 3 until the target portion of the biological sample S is exposed. Further, the control unit 5 may automatically determine whether the target portion of the biological sample S reaches an exposed state based on the vertical illumination image imaged by the imaging part 30, or may display the vertical illumination image on the display part 32 to allow an operator to determine whether the target portion of the biological sample S reaches the exposed state.

Next, the control unit 5 cuts the embedding block B by a predetermined thickness (step S113). That is, the control unit 5 causes the height change part 51 to perform the delivery of the embedding block B by the predetermined thickness and performs the cutting, and cuts out thin slices having the predetermined thickness. Further, the cut-out thin slices are expanded while floating on a surface of at least water (liquid) and the expanded thin slices are transferred onto a slide glass to manufacture thin slice samples.

After termination of the process of step S113, the thin-slice manufacturing device 1 terminates the thin slice manufacturing process.

As described above, the thin-slice manufacturing device 1 according to the present embodiment cuts the embedding block B in which the biological sample S (the sample) is embedded in the paraffin P (the embedding agent) using the cutting blade 3 relatively moving with respect to the embedding block B along the virtual plane H to cut out thin slices. The thin-slice manufacturing device 1 according to the present embodiment includes the vertical illumination part 4 and the inclination estimation part 54. The vertical illumination part 4 radiates the parallel light to the embedding block B. Then, the inclination estimation part 54 detects the boundary line between the cutting surface cut along the virtual plane H and the non-cutting surface based on reflection of light by the light radiated to the embedding block B by the vertical illumination part 4, and estimates the inclination information indicating information related to the inclination of the embedding block B based on the detected boundary line.

Accordingly, since the thin-slice manufacturing device 1 according to the present embodiment can estimate the inclination information of the embedding block B based on the boundary line between the cutting surface and the non-cutting surface, for example, the surface matching (surface matching process) of the cutting surface can be performed without the necessity of the position detection of the embedding block B by the sensor, and simultaneously, thin slices having an appropriate cross section can be manufactured. In addition, in the thin-slice manufacturing device 1 according to the present embodiment, for example, the surface shaping can be appropriately performed even when the cross section of the tissue of the biological sample S embedded in the embedding block B is inclined with respect to the cutting surface, and the thin slices having an appropriate cross section can be manufactured.

In addition, for example, in the surface matching process of the related art, a technique of adjusting the inclination of the embedding block B such that the brightness of the vertical illumination image is maximized is known. However, in this technology, it cannot determine the direction of the inclination of the embedding block B, and therefore, the surface matching process may be time-consuming.

On the other hand, since the thin-slice manufacturing device 1 according to the present embodiment can estimate the inclination information (for example, the direction of the inclination and the degree of inclination) of the embedding block B by the vertical illumination part 4, in comparison with the surface matching process of the related art, time required for the surface matching process can be reduced.

In addition, in the present embodiment, the inclination information includes the direction of the inclination and the degree of inclination. Then, the inclination estimation part 54 estimates the direction of the inclination based on the normal vector of the boundary line, and simultaneously, estimates the degree of inclination based on the movement amount of the boundary line when the virtual plane H is moved by the predetermined amount in the direction perpendicular to the virtual plane H in order to perform the cutting, and based on the predetermined amount.

Accordingly, the thin-slice manufacturing device 1 according to the present embodiment can appropriately estimate the direction of the inclination and the degree of inclination (the inclination angle) serving as the inclination information by using a simple means.

In addition, in the present embodiment, the movement amount of the boundary line is a movement amount in a direction of the normal vector. In addition, the inclination estimation part 54 calculates the degree of inclination (the inclination angle $\theta$) based on the movement amount ($\Delta$BL) of the boundary line, the predetermined amount (the thickness $\Delta$Ts) in the direction perpendicular to the virtual plane H, and a predetermined trigonometric function.

Accordingly, the thin-slice manufacturing device 1 according to the present embodiment can calculate the movement amount of the boundary line, and simultaneously, can appropriately calculate the degree of inclination using a simple means.

In addition, in the present embodiment, the normal vector of the boundary line is an average normal vector.

Accordingly, the inclination estimation part 54 can appropriately estimate the inclination information (the direction of the inclination and the degree of inclination (inclination angle)), for example, even when the boundary line is a curve.

In addition, the thin-slice manufacturing device 1 according to the present embodiment includes the inclination compensation part 55 (the compensation part) configured to compensate the inclination of the embedding block B based on the inclination information estimated by the inclination estimation part 54. The inclination compensation part 55 compensates the inclination of the embedding block B so that the predetermined cross section of the embedding block B and the virtual plane H are parallel to each other based on the inclination information estimated by the inclination estimation part 54.

Accordingly, the thin-slice manufacturing device 1 according to the present embodiment can appropriately perform the surface matching (surface matching process) of the cutting surface. For this reason, the thin-slice manufacturing device 1 according to the present embodiment can appropriately manufacture the thin slices having an appropriate cross section.

In addition, in the present embodiment, the above-mentioned boundary line includes the boundary line between the cutting surface and the non-cutting surface of the paraffin P, and the predetermined cross section of the embedding block B includes the roughly cut surface representing a predetermined cutting surface on which the rough cutting, which cuts the surface to the predetermined cutting surface in advance, is performed. Then, the inclination compensation part 55 compensates the inclination of the embedding block B so that the roughly cut surface and the virtual plane H are parallel to each other based on the inclination information.

Accordingly, for example, since the thin-slice manufacturing device 1 according to the present embodiment can appropriately perform the surface matching process with respect to the roughly cut surface previously cut by the operator, the thin slices having an appropriate cross section can be manufactured based on the roughly cut surface.

In addition, the thin-slice manufacturing device 1 of the present embodiment includes the inclination angle change part 52 configured to change the inclination of the block holder configured to fix the embedding block B, and the imaging part 30 configured to image an image of the embedding block B by reflection of the light in a state in which the parallel light is radiated from the vertical illumination part 4. In addition, the inclination estimation part 54 detects the boundary line based on the image imaged by the imaging part 30, and estimates the inclination information based on the detected boundary line. Then, the inclination compensation part 55 changes the inclination of the block holder 13 using the inclination angle change part 52 based on the inclination information.

Accordingly, since the boundary line is detected based on the image imaged by the imaging part 30, the vertical illumination part 4 can accurately detect the boundary line by the image processing. For this reason, the thin-slice manufacturing device 1 of the present embodiment can appropriately perform the surface matching process. In addition, the thin-slice manufacturing device 1 of the present embodiment can appropriately manufacture the thin slices having an appropriate cross section.

Further, according to the present embodiment, the thin-slice manufacturing method is a thin-slice manufacturing method of cutting the embedding block B in which the biological sample S is embedded in the paraffin P using the cutting blade 3 relatively moving with respect to the embedding block B along the virtual plane H to cut out thin slices. The thin-slice manufacturing method includes a radiation step and an estimation step. In the radiation step, the vertical illumination part 4 radiates the parallel light to the embedding block B. Then, in the estimation step, the inclination estimation part 54 detects the boundary line between the cutting surface cut along the virtual plane H and the non-cutting surface based on reflection of the light generated by the parallel light radiated by the embedding block B in the radiation step, and estimates the inclination information showing the information related to the inclination of the embedding block B based on the detected boundary line.

Accordingly, like the thin-slice manufacturing device 1, for example, the thin-slice manufacturing method according to the present embodiment can perform the surface matching (the surface matching process) of the cutting surface without the necessity of the position detection of the embedding block B by the sensor, and simultaneously, can manufacture the thin slice having an appropriate cross section.

Next, the thin-slice manufacturing device 1 according to a second embodiment of the present invention will be described with reference to the accompanying drawings.

Second Embodiment

In the above-mentioned first embodiment, the surface matching process of estimating the inclination information of the roughly cut surface and compensating the inclination of the embedding block B based on the estimated inclination information of the roughly cut surface has been described. In the present embodiment, a case in which inclination information of a predetermined cross section of the biological sample S is estimated and inclination of the embedding block B is compensated based on the estimated inclination information of the predetermined cross section of the biological sample S will be described.

Further, in the present embodiment, a case in which the predetermined cross section of the biological sample S is a surface of the biological sample S will be described.

Further, in the present embodiment, since a basic configuration of the thin-slice manufacturing device 1 is the same as the first embodiment shown in FIG. 1, description thereof will be omitted.

In the present embodiment, the boundary line includes the boundary line between the cutting surface and the non-cutting surface of the biological sample S, and the predetermined cross section of the embedding block B includes a predetermined cross section of the biological sample S (for example, a surface of the biological sample S). In addition, the inclination compensation part 55 according to the present embodiment compensates the inclination of the embedding block B so that the predetermined cross section of the biological sample S and the virtual plane H are parallel to each other based on the inclination information (the direction of the inclination of the biological sample S and the degree of inclination (the inclination angle)).

Figure 10:
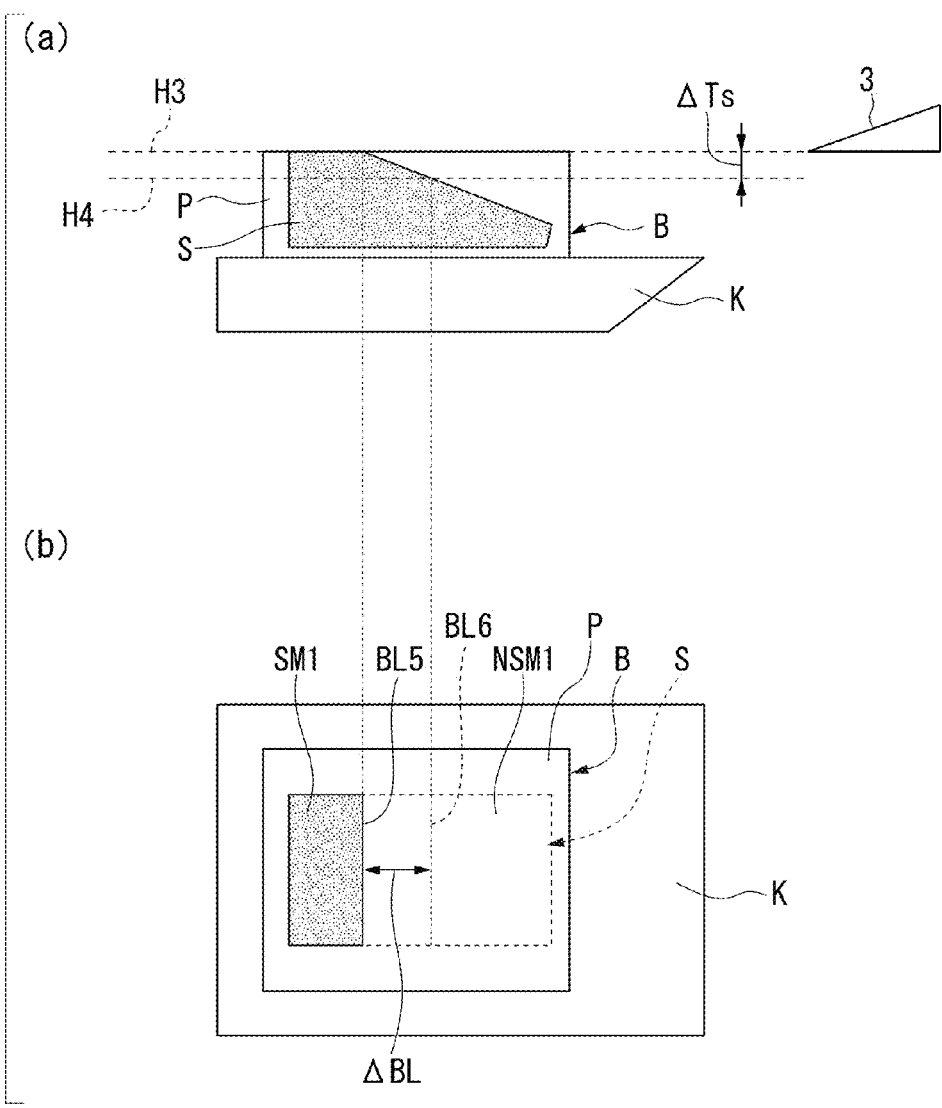
FIG. 10 is a view showing a detection example of an inclination angle of a biological sample according to a second embodiment.

Further, when the vertical illumination is radiated to the embedding block B in which the biological sample S is exposed, as shown in FIG. 10(*b*) to be described below, the cutting surface of the biological sample S is observed darker and the non-cutting surface (the uncut surface) is observed brighter. Here, the non-cutting surface (the uncut surface) has a cross section of the paraffin P in which the biological sample S is still not exposed.

Next, an operation of the thin-slice manufacturing device 1 according to the present embodiment will be described with reference to the accompanying drawings. In the present embodiment, the operation when the surface matching process (surface shaping process) is performed with respect to the surface of the biological sample S will be described.

Here, first, a process of estimating a direction of the inclination of the biological sample S by the inclination estimation part 54 will be described.

<Estimation Process of Direction of Inclination in Organism Sample S>

The inclination estimation part 54 according to the present embodiment detects the boundary line between the cutting surface and the non-cutting surface of the biological sample S by a variation in brightness of the vertical illumination image imaged by the imaging part 30, and the normal vector calculation part 53 calculates a normal vector of the detected boundary line. Then, the inclination estimation part 54 estimates the direction of the normal vector calculated by the normal vector calculation part 53 as the direction of the inclination of the biological sample S.

Next, a process of estimating the degree of inclination (the inclination angle) of the biological sample S by the inclination estimation part 54 will be described with reference to FIG. 10.

<Estimation Process of Degree of Inclination (Inclination Angle) in Organism Sample S>

FIG. 10 is a view showing a detection example of an inclination angle of the biological sample S according to the present embodiment.

FIG. 10(*a*) is a cross-sectional view of the embedding block B fixed onto the cassette K and cut until the biological sample S is exposed. In addition, FIG. 10(*a*) shows a state that, after the cutting blade 3 cuts the embedding block B along the virtual plane H3, the cutting blade 3 is delivered by the predetermined amount (the thickness ΔTs) in the Z direction, and the cutting blade 3 cuts the embedding block B along the virtual plane H4.

In addition, FIG. 10(*b*) shows a state, as shown in FIG. 10(*a*), of the embedding block B observed by the imaging part 30 when the vertical illumination part 4 radiates the vertical illumination after the cutting blade 3 cuts the embedding block B along the virtual plane H3.

In FIG. 10, a boundary line BL5 shows a boundary line (a boundary line upon this cutting) between a cutting surface SM1 and a non-cutting surface NSM1 of the biological sample S after the cutting blade 3 cuts the embedding block B along the virtual plane H3. In addition, a boundary line BL6 shows a boundary line (a boundary line upon the next cutting) between the cutting surface and the non-cutting surface of the biological sample S after the cutting blade 3 cuts the embedding block B along the virtual plane H4.

The inclination estimation part 54 acquires the vertical illumination image imaged by the imaging part 30 after cutting along the virtual plane H3 by the cutting blade 3 and the vertical illumination image after cutting along the virtual plane H4 by the cutting blade 3 from the imaging part 30. The inclination estimation part 54 detects the boundary lines BL5 and BL6 between the cutting surface and the non-cutting surface and calculates the movement amount ΔBL of the boundary line based on a variation in brightness of the vertical illumination image acquired by the imaging part 30. Here, the movement amount ΔBL of the boundary line is a movement amount in a direction of the normal vector. The inclination estimation part 54 calculates the inclination angle θ of the biological sample S using the above-mentioned equation (1) based on the calculated movement amount ΔBL of the boundary line and the predetermined amount (the thickness ΔTs).

In this way, for example, the inclination estimation part 54 estimates the degree of inclination (the inclination angle θ) of the biological sample S based on the movement amount ΔBL of the boundary line when the virtual plane is moved by the predetermined amount (the thickness ΔTs) in the direction perpendicular to virtual planes (H3 and H4) in order to perform cutting, and based on the predetermined amount (the thickness ΔTs).

Next, a thin slice manufacturing process operation of the thin-slice manufacturing device 1 according to the second embodiment will be described with reference to FIG. 11.

<Operation Procedure of Thin Slice Manufacturing Process>

Figure 11:
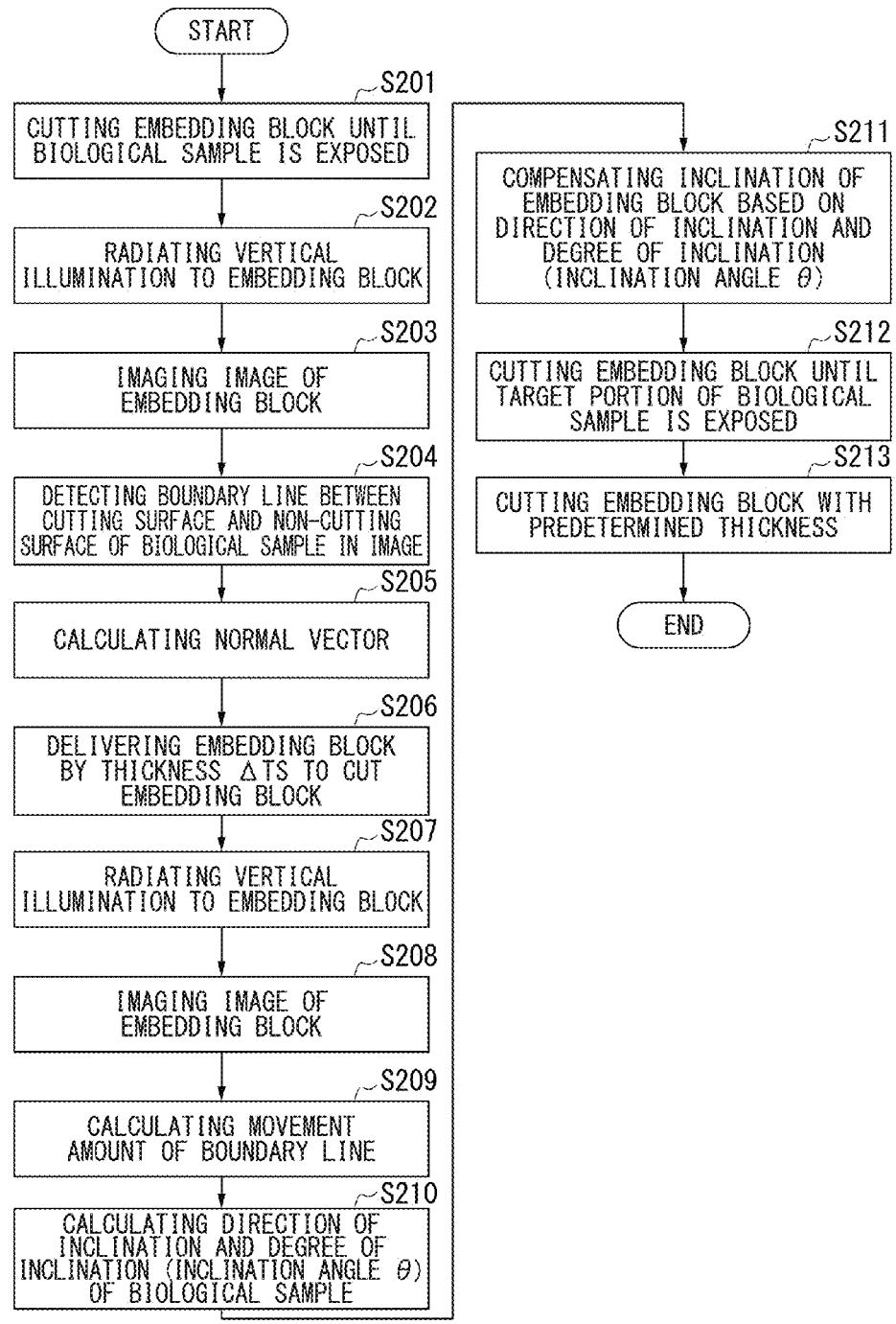
FIG. 11 is a flowchart showing an example of an operation of a thin-slice manufacturing device according to the second embodiment.

FIG. 11 is a flowchart showing an example of an operation of the thin-slice manufacturing device 1 according to the present embodiment.

In FIG. 11, the embedding block B is set on the support frame 10 of the base section 2 via the block holder 13. The thin-slice manufacturing device 1 starts the thin slice manufacturing process in a state in which the swing mechanism part 11 is in an initial state (X=0, Y=0) and the support frame 10 is horizontally disposed. Further, for example, the embedding block B is in a state in which the embedding block B is not previously roughly cut.

First, the thin-slice manufacturing device 1 cuts the embedding block B until the biological sample S is exposed (step S201). That is, the control unit 5 causes the height change part 51 to repeatedly perform the process of delivering the embedding block B by a predetermined thickness and cutting the embedding block B with the cutting blade movement mechanism part 15 including the cutting blade 3 until the biological sample S is exposed. Further, the control unit 5 may automatically determine whether the biological sample S reaches an exposed state based on the vertical illumination image imaged by the imaging part 30 or display the vertical illumination image on the display part 32 to allow an operator to determine whether a target portion of the biological sample S reaches an exposed state.

Next, the vertical illumination part 4 radiates vertical illumination to the embedding block B (step S202), and the imaging part 30 images an image of the embedding block B (step S203).

Next, the inclination estimation part 54 of the control unit 5 detects the boundary line between the cutting surface and the non-cutting surface of the biological sample S in the image (step S204). The inclination estimation part 54 acquires the vertical illumination image from the imaging part 30, and detects the boundary line between the cutting surface (an exposure surface) and the non-cutting surface (a non-exposure surface) of the biological sample S based on the brightness of the acquired vertical illumination image.

Next, the normal vector calculation part 53 of the control unit 5 calculates the normal vector of the boundary line (step S205). That is, the normal vector calculation part 53 calculates the normal vector of the boundary line based on the boundary line between the cutting surface and the non-cutting surface of the biological sample S detected by the inclination estimation part 54.

Next, since the processing from step S206 to step S209 is the same as the processing from step S106 to step S109 according to the first embodiment shown in FIG. 9, description thereof will be omitted.

Next, in step S210, the inclination estimation part 54 calculates the direction of the inclination of the biological sample S and the degree of inclination (the inclination angle θ). Specifically, the inclination estimation part 54 calculates the direction of the inclination of the biological sample S based on the normal vector calculated by the normal vector calculation part 53 in step S205. In addition, the inclination estimation part 54 calculates the degree of inclination (the inclination angle θ) of the biological sample S using the above-mentioned equation (1) based on the movement amount ΔBL of the boundary line calculated in step S209 and the thickness ΔTs.

Next, the inclination compensation part 55 of the control unit 5 compensates the inclination of the embedding block B based on the direction of the inclination and the degree of inclination (the inclination angle θ) of the biological sample S (step S211). Specifically, the inclination compensation part 55 compensates the inclination of the embedding block B so that the surface of the biological sample S (a cross section parallel to the surface of the embedded organism sample S) and the virtual plane H are parallel to each other based on the inclination information (the direction of the inclination and the inclination angle of the biological sample S). The inclination compensation part 55 changes the inclination of the block holder 13 and the support frame 10 with respect to the inclination angle change part 52. That is, the inclination angle change part 52 controls the swing mechanism part 11 (the Y-axis swing mechanism part 11a and the X-axis swing mechanism part 11b), and changes the inclination of the block holder 13 and the inclination of the support frame 10 so that the surface of the biological sample S and the virtual plane H are parallel to each other.

Next, the control unit 5 cuts the embedding block B until a target portion of the biological sample S is exposed (step S212). That is, the control unit 5 causes the height change part 51 to repeat the processing of delivering the embedding block B by a predetermined thickness and cutting the embedding block B by the cutting blade movement mechanism part 15 with the cutting blade 3 until the target portion of the biological sample S is exposed.

Further, the control unit 5 may automatically determine whether the target portion of the biological sample S reaches an exposed state based on the vertical illumination image imaged by the imaging part 30 or may display the vertical illumination image on the display part 32 to allow an operator to determine whether the target area of the biological sample S reaches the exposed state.

Next, the control unit 5 cuts the embedding block B by a predetermined thickness (step S213). That is, the control unit 5 causes the height change part 51 to deliver the embedding block B by a predetermined thickness to perform the cutting to cut out the thin slices having a predetermined thickness. Further, the cut-out thin slices are submerged in at least water (liquid) to be expanded, and the expanded thin slices are transferred onto the slide glass to manufacturing thin slice samples.

After termination of the process of step S213, the thin-slice manufacturing device 1 terminates the thin slice manufacturing process.

As described above, according to the present embodiment, the boundary line includes the boundary line between the cutting surface and the non-cutting surface of the biological sample S, and the predetermined cross section of the embedding block B includes the predetermined cross section of the biological sample S (for example, the surface of the embedded organism sample S). The inclination estimation part 54 calculates the direction of the inclination and the degree of inclination (the inclination angle θ) of the biological sample S based on the boundary line between the cutting surface and the non-cutting surface of the biological sample S. Then, the inclination compensation part 55 compensates the inclination of the embedding block B so that the predetermined cross section of the biological sample S and the virtual plane H are parallel to each other based on the inclination information.

Accordingly, the thin-slice manufacturing device 1 according to the present embodiment can appropriately perform the surface matching (the surface shaping process) of the cutting surface, for example, even when the cutting surface of the embedding block does not coincide with the cross section of the biological sample appropriate for inspection or observation. Accordingly, the thin-slice manufacturing device 1 according to the present embodiment can manufacture the thin slices having an appropriate cross section.

In addition, since the thin-slice manufacturing device 1 according to the present embodiment can estimate the inclination information of the embedding block B based on the boundary line between the cutting surface and the non-cutting surface of the biological sample S, like the first embodiment, for example, the surface matching (the surface shaping process) of the cutting surface can be performed without the necessity of the position detection of the embedding block B by the sensor.

Next, the thin-slice manufacturing device 1 according to a third embodiment of the present invention will be described with reference to the accompanying drawings.

Third Embodiment

In the present embodiment, the case in which the surface matching process according to the first embodiment and the surface shaping process according to the second embodiment are selectively performed will be described. That is, the thin-slice manufacturing device 1 according to the present embodiment performs the surface matching process of compensating the inclination of the embedding block B based on the inclination information of the roughly cut surface when the surface shaping (the rough cutting) is performed on the embedding block B. In addition, the thin-slice manufacturing device 1 according to the present embodiment compensates the inclination of the embedding block B based on the inclination information of the predetermined cross section of the biological sample S when the surface shaping is not performed on the embedding block B.

Figure 12:
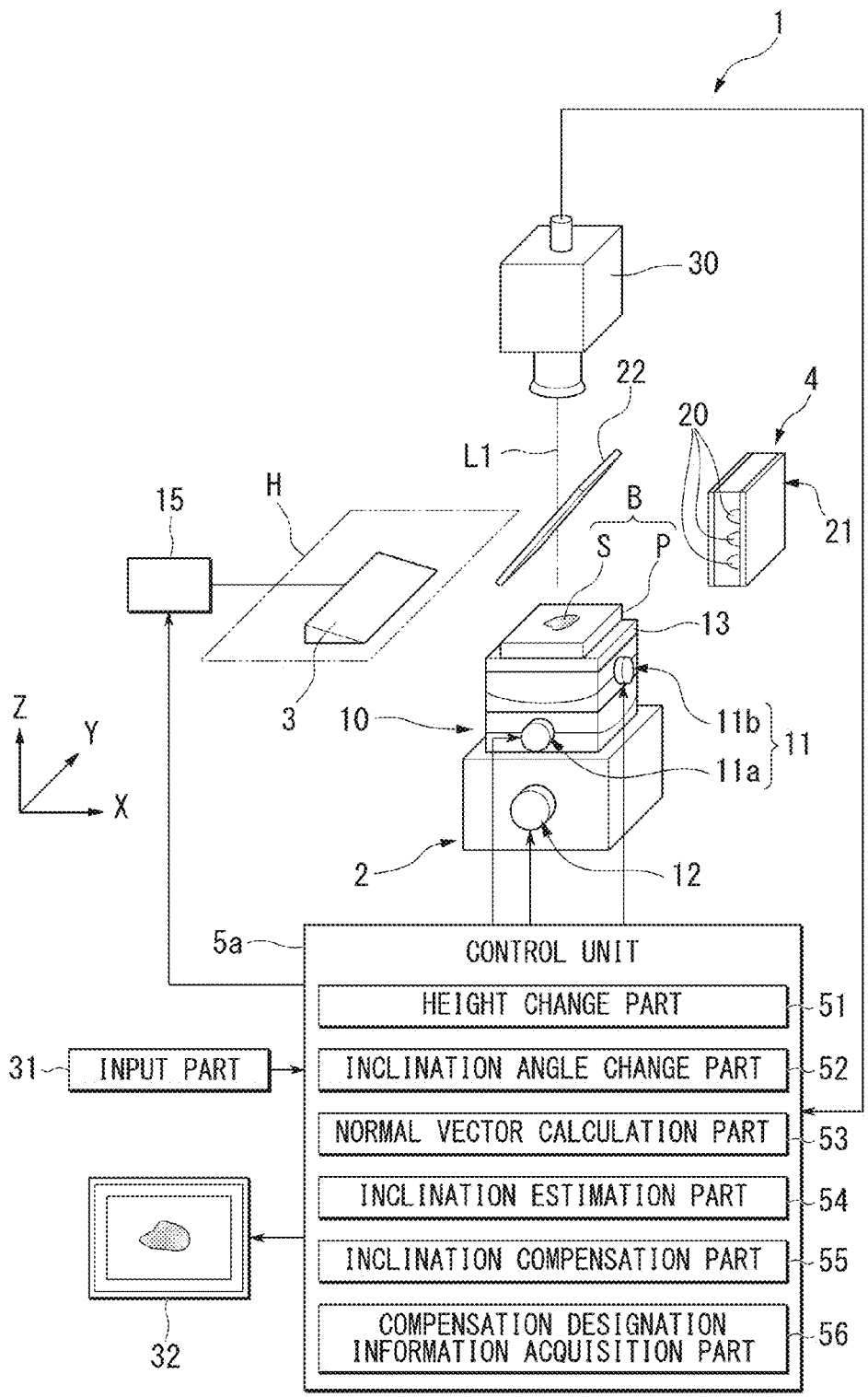
FIG. 12 is a block diagram showing an example of a thin-slice manufacturing device according to a third embodiment.

FIG. 12 is a block diagram showing an example of the thin-slice manufacturing device 1 according to the third embodiment.

In FIG. 12, the thin-slice manufacturing device 1 includes the base section 2, the cutting blade 3, the vertical illumination part 4, a control unit 5a, the imaging part 30, the input part 31 and the display part 32. In addition, the control unit 5a includes the height change part 51, the inclination angle change part 52, the normal vector calculation part 53, the inclination estimation part 54, the inclination compensation part 55 and a compensation designation information acquisition part 56.

Further, in FIG. 12, the same components as shown in FIG. 1 are designated by the same reference numerals, and description thereof will be omitted.

The present embodiment is distinguished from the first embodiment and the second embodiment in that the control unit 5a includes the compensation designation information acquisition part 56, and hereinafter, the compensation designation information acquisition part 56 will be described.

The compensation designation information acquisition part 56 acquires the compensation designation information that is input from the input part 31 and designates whether the rough cutting is performed on the embedding block B. That is, the compensation designation information acquisition part 56 acquires the above-mentioned compensation designation information input by an operator via the input part 31.

Further, the control unit 5a according to the present embodiment performs the surface matching or the surface shaping process with respect to the inclination estimation part 54 and the inclination compensation part 55 based on the compensation designation information acquired by the compensation designation information acquisition part 56.

Specifically, when the compensation designation information acquisition part 56 acquires the information showing that the surface shaping (the rough cutting) is performed on the embedding block B as the compensation designation information, as described in the first embodiment, the inclination estimation part 54 estimates the inclination information of the roughly cut surface based on the boundary line between the cutting surface and the non-cutting surface of the paraffin P. Then, as described in the first embodiment, the inclination compensation part 55 compensates the inclination of the embedding block B based on the inclination information of the roughly cut surface estimated by the inclination estimation part 54, i.e., the inclination compensation part 55 compensates the inclination of the embedding block B so that the roughly cut surface and the virtual plane H are parallel to each other.

In addition, as described in the second embodiment, when the compensation designation information acquisition part 56 acquires the information showing that the surface shaping is not performed on the embedding block B as the compensation designation information, the inclination estimation part 54 estimates the inclination information of the biological sample S based on the boundary line between the cutting surface and the non-cutting surface of the biological sample S. Then, as described in the second embodiment, the inclination compensation part 55 compensates the inclination of the embedding block B based on the inclination information of the biological sample S estimated by the inclination estimation part 54, i.e., the inclination compensation part 55 compensates the inclination of the embedding block B so that the predetermined cross section of the biological sample S and the virtual plane H are parallel to each other.

Next, the thin slice manufacturing process operation of the thin-slice manufacturing device 1 according to the third embodiment will be described with reference to FIG. 13.

<Operation Procedure of Thin Slice Manufacturing Process>

Figure 13:
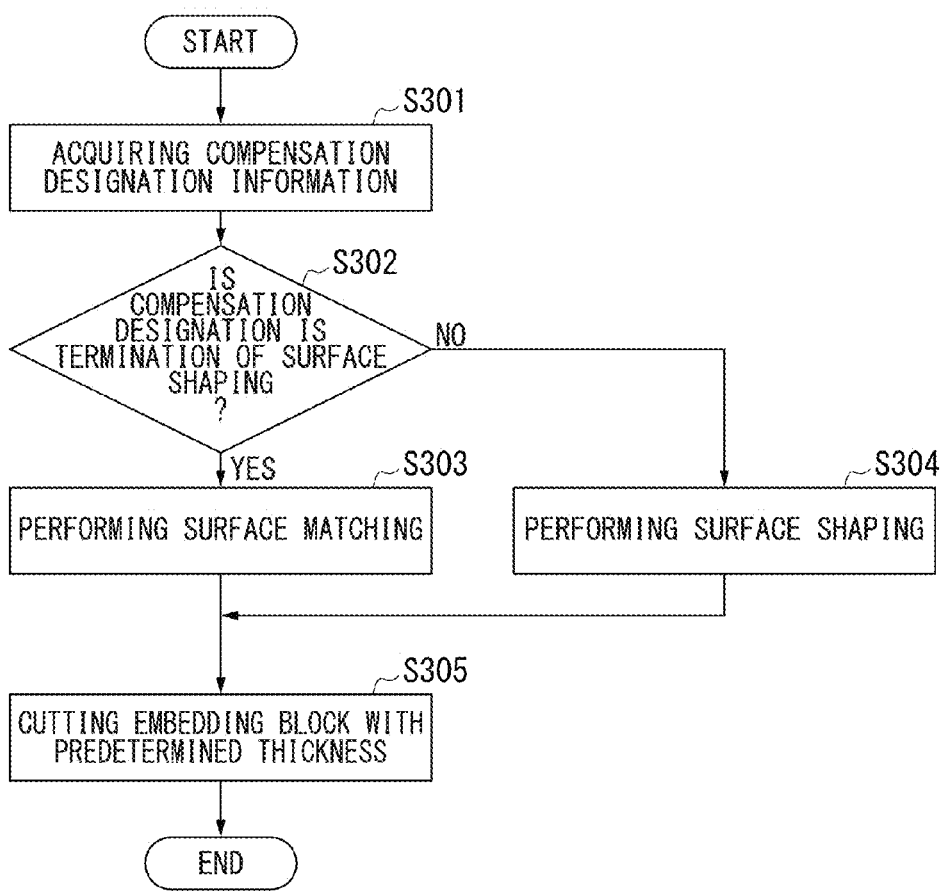
FIG. 13 is a flowchart showing an example of an operation of the thin-slice manufacturing device according to the third embodiment.

FIG. 13 is a flowchart showing an example of an operation of the thin-slice manufacturing device 1 according to the present embodiment.

In FIG. 13, the embedding block B is set on the support frame 10 of the base section 2 via the block holder 13, and the thin-slice manufacturing device 1 starts the thin slice manufacturing process in a state in which the swing mechanism part 11 is in an initial state (X=0, Y=0) and the support frame 10 is horizontally disposed. Further, in the present embodiment, the embedding block B is in a state in which the surface shaping (the rough cutting) has been previously performed or in a state in which the surface shaping (the rough cutting) has not been previously performed, and whether the surface shaping (the rough cutting) has been previously performed is designated by an operator via the input part 31.

First, the thin-slice manufacturing device 1 acquires the compensation designation information (step S301). For example, the control unit 5 displays a request to an operator such that the compensation designation information of determining whether the surface shaping (rough cutting) has been previously performed on the embedding block B is input into the display part 32. The compensation designation information acquisition part 56 of the control unit 5 acquires the compensation designation information input from the operator via the input part 31.

Next, the control unit 5 determines whether the compensation designation information is the surface shaping termination (step S302). That is, the control unit 5 determines whether the compensation designation information acquired by the compensation designation information acquisition part 56 is information that the surface shaping has been previously performed on the embedding block B. The control unit 5 advances the processing to step S303 when the surface shaping has been previously performed on the embedding block B (step S302: YES). In addition, the control unit 5 advances the processing to step S304 when the surface shaping has not been previously performed on the embedding block B (step S302: NO).

In step S303, the control unit 5 performs the surface matching. That is, the control unit 5 performs the processing from step S101 to step S112 shown in FIG. 9 and performs the surface matching on the roughly cut surface.

In addition, in step S304, the control unit 5 performs the surface shaping. That is, the control unit 5 performs the processing from step S201 to step S212 shown in FIG. 11. Further, the surface shaping process by the control unit 5 includes the inclination compensation of the end surface of the biological sample S.

In addition, next, since the processing of step S305 is the same as the processing of step S113 shown in FIG. 9 (the processing of step S213 shown in FIG. 11), and description thereof will be omitted.

As described above, according to the present embodiment, the thin-slice manufacturing device 1 includes the compensation designation information acquisition part 56 configured to acquire the compensation designation information that designates whether the surface shaping (the rough cutting) has been performed on the embedding block B. In addition, the inclination compensation part 55 compensates the inclination of the embedding block B so that the roughly cut surface and the virtual plane H are parallel to each other based on the inclination information of the roughly cut surface when the surface shaping (the rough cutting) is performed on the embedding block B. In addition, the inclination compensation part 55 compensates the inclination of the embedding block B so that the predetermined cross section of the biological sample S and the virtual plane H are parallel to each other based on the inclination information of the biological sample S when the surface shaping (the rough cutting) is not performed on the embedding block B.

Accordingly, the thin-slice manufacturing device 1 according to the present embodiment can appropriately perform the surface matching (the surface matching process) of the cutting surface according to a state of the embedding block B.

In the present embodiment, the case in which the compensation designation information acquisition part 56 acquires the compensation designation information from the input part 31 has been described. However, the control unit 5 may include a determination part configured to determine whether the surface shaping (the rough cutting) has been performed on the embedding block B based on the image imaged by the imaging part 30, and acquire the compensation designation information from the determination part.

Further, the aspect of the present invention is not limited to the above-mentioned embodiments but may be modified without departing from the spirit of the present invention.

Figure 14:
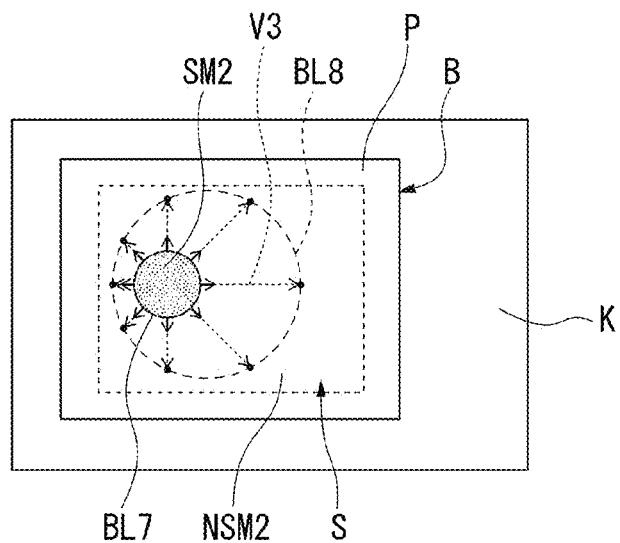
FIG. 14 is a first view showing another example of a calculation method of a normal vector.

For example, the normal vector calculation part 53 may calculate the normal vector of the boundary line based on an extended normal vector as shown in FIG. 14.

FIG. 14 is a first view showing another example of a calculation method of a normal vector.

In FIG. 14, a boundary line BL7 shows a boundary line (a boundary line at Nth cutting) between a cutting surface SM2 and a non-cutting surface NSM2 of the biological sample S after the cutting blade 3 cuts the embedding block B Nth times along the virtual plane H. Here, the embedding block B is fixed onto the cassette K, the cutting surface SM2 is a tissue surface of the biological sample S, and the non-cutting surface NSM2 is the paraffin P.

A boundary line BL8 shows a boundary line (a boundary line upon an (N+m)th cutting) between the cutting surface and the non-cutting surface of the biological sample S after the cutting blade 3 cuts the embedding block B (N+m)th times along the virtual plane H.

In the case shown in FIG. 14, the normal vector calculation part 53 may calculate the maximum extended normal vector V3 of the extension normal vector obtained by extending the normal vector of the boundary line BL7 to the boundary line BL8 of (N+m)th times as the normal vector of the boundary line. That is, the normal vector of the boundary line may be a vector having a largest magnitude in the vector in a normal direction of the boundary line having the movement amount of the boundary line as a magnitude. In this case, the inclination estimation part 54 estimates the direction of the inclination and the degree of inclination (the inclination angle) of the biological sample S based on the maximum extended normal vector V3. Accordingly, the inclination estimation part 54 can appropriately estimate the inclination information (the direction of the inclination and the degree of inclination (the inclination angle)), for example, even when the boundary line is a curve (as shown in FIG. 14, even when the boundary line is a circle).

Further, in an example shown in FIG. 14, the normal vector calculation part 53 uses the maximum extended normal vector as the normal vector of the boundary line.

However, an average vector of the extended normal vector may be used as the normal vector of the boundary line.

In addition, in the example shown in FIG. 14, while the case applied to the second embodiment has been described, the case may be similarly applied to the first embodiment.

In addition, in the above-mentioned embodiments, the case in which the thin-slice manufacturing device 1 detects the boundary line between the cutting surface and the non-cutting surface based on reflection of the light obtained by radiating the vertical illumination to the embedding block B has been described. However, the radiated illumination is not limited to the vertical illumination. For example, the light may be radiated to the embedding block B in an inclined manner, or another illumination may be radiated to the embedding block B as long as the illumination can detect the boundary line between the cutting surface and the non-cutting surface. In addition, when the light is radiated to the embedding block B in an inclined manner, the imaging part 30 may be disposed on an optical axis on which the light radiated to the embedding block B is reflected by the surface of the embedding block B or the cutting surface.

In addition, in the above-mentioned embodiments, the thin-slice manufacturing device 1 may include a light source such as diffuse light or the like in addition to the vertical illumination, and the images imaged by radiating different illuminations may be combined to be displayed on the display part 32.

Figure 15:
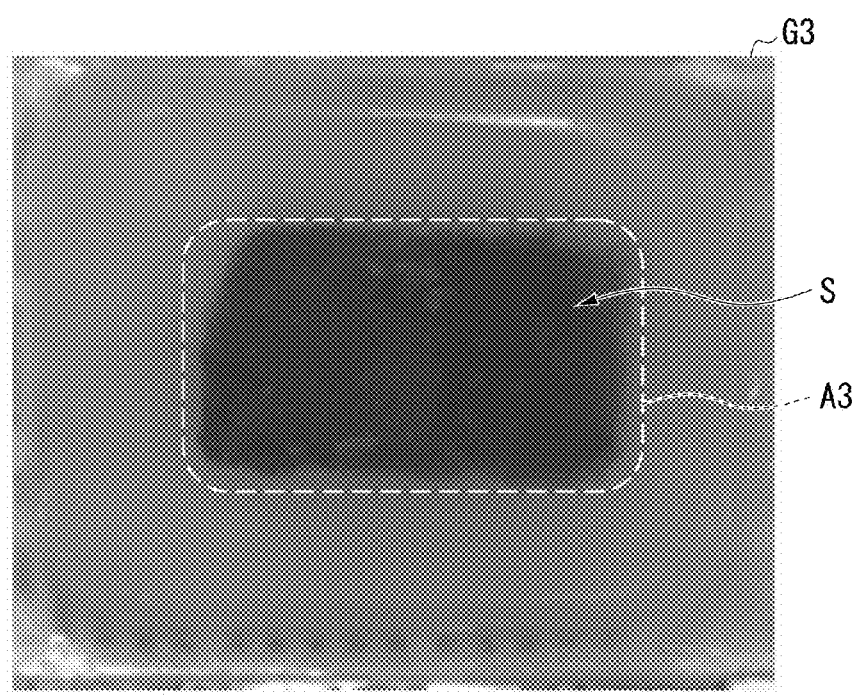
FIG. 15 is a view showing an example of a diffused light illumination image of an embedding block according to the present embodiment.
Figure 16:
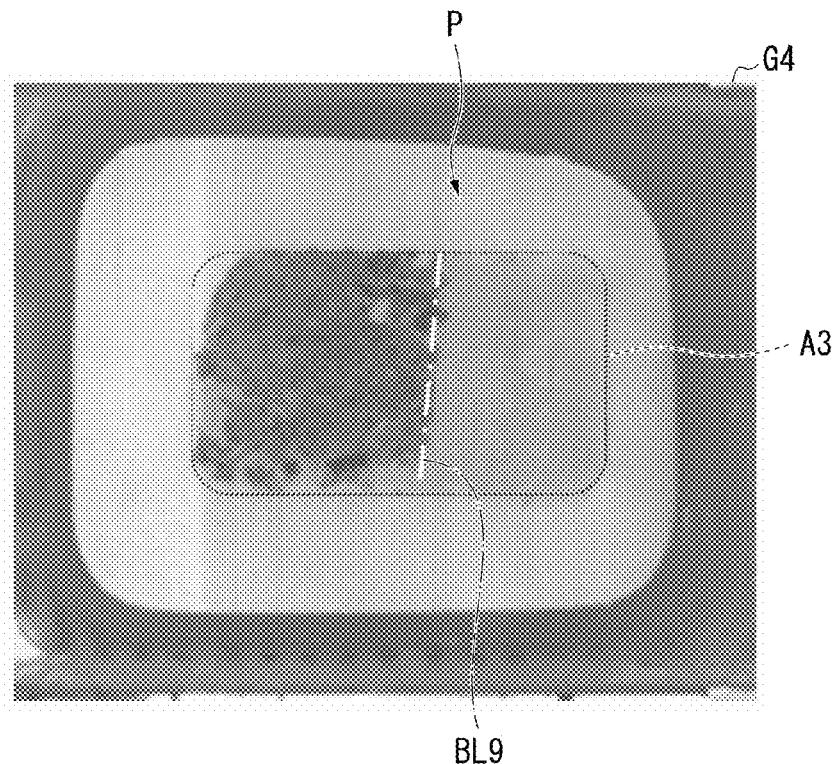
FIG. 16 is a third view showing an example of a vertical illumination image of the embedding block according to the present embodiment.

In addition, for example, when the thin-slice manufacturing device 1 includes the vertical illumination part 4 and a diffuse light illumination part (not shown) as an illumination part and the radiation part switches and radiates the vertical illumination light and the diffuse light (conventional illumination light) to the embedding block, the image is imaged as shown in FIGS. 15 and 16.

FIG. 15 is a view showing an example of the diffuse light illumination image of the embedding block according to the present embodiment.

In FIG. 15, an image G3 shows a diffuse light illumination image (a conventional illumination image) imaged by radiating diffuse light (conventional illumination light) to the embedding block B. In the image G3, since the diffuse light is radiated, a contour (an outline) of the biological sample S (the tissue) in the embedding block B can be determined, and an area A3 shows the contour (the outline) of the biological sample S. The inclination estimation part 54 extracts the outline of the biological sample S based on, for example, a variation in brightness of the diffuse light illumination image such as the image G3.

In addition, FIG. 16 is a third view showing an example of the vertical illumination image of the embedding block according to the present embodiment.

In FIG. 16, an image G4 shows a vertical illumination image (a conventional illumination image) imaged by radiating the vertical illumination light to the same embedding block B having a diffuse light illumination image in FIG. 15. In the image G4, the area A3 shows the contour (the outline) of the biological sample S embedded in the paraffin P, and a boundary line BL9 shows the boundary line between the cutting surface (the exposure surface) and the non-cutting surface (the non-exposure surface) of the biological sample S. In this case, the inclination estimation part 54 detects the boundary line BL9 between the cutting surface and the non-cutting surface based on a variation in brightness of the vertical illumination image acquired from the imaging part 30.

Figure 17:
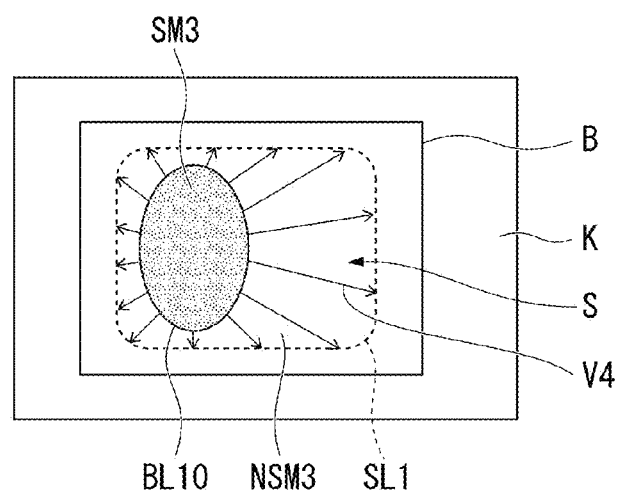
FIG. 17 is a second view showing another example of the calculation method of the normal vector.

As shown in FIGS. 15 and 16, as the vertical illumination light and the diffuse light are switched to be radiated to the embedding block B to image the image, for example, as shown in FIG. 17, the normal vector calculation part 53 may calculate the normal vector of the boundary line based on the extension normal vector.

FIG. 17 is a second view showing another example of a calculation method of a normal vector.

In FIG. 17, the boundary line BL10 shows a boundary line between a cutting surface SM3 and a non-cutting surface NSM3 of the biological sample S after the cutting blade 3 cuts the embedding block B along the virtual plane H. Here, the embedding block B is fixed onto the cassette K, the cutting surface SM3 is a tissue surface of the biological sample S, and the non-cutting surface NSM3 is the paraffin P.

In addition, as shown in FIG. 15, an outline SL1 shows an outline of the biological sample S obtained based on radiation of the diffuse light.

In the case as shown in FIG. 17, the normal vector calculation part 53 may calculate the maximum extended normal vector V4 of the extended normal vector in which the normal vector of the boundary line BL10 is extended to the outline SL1 of the biological sample S as the normal vector of the boundary line. That is, the normal vector of the boundary line may be a vector having a largest magnitude among the vector in the normal direction of the boundary line BL10 in which a magnitude thereof is set as a length until to the outline SL1 of the biological sample S obtained based on radiation of the diffuse light.

In this case, the radiation part switches and radiates the vertical illumination light and the diffuse light to the embedding block, and the inclination estimation part 54 detects the boundary line BL10 based on reflection of the vertical illumination light. Then, the inclination estimation part 54 estimates the direction of the inclination and the degree of inclination (the inclination angle) of the biological sample S based on the maximum extended normal vector V4. Accordingly, for example, the inclination estimation part 54 can appropriately estimate the inclination information (the direction of the inclination and the degree of inclination (the inclination angle)) even when the boundary line is a curve (as shown in FIG. 17, even when the boundary line is a circle).

Further, in an example shown in FIG. 17, the normal vector calculation part 53 uses the maximum extended normal vector as the normal vector of the boundary line. However, an average vector of the extended normal vector may be used as the normal vector of the boundary line.

In addition, in the example shown in FIG. 17, while the case applied to the second embodiment has been described, the case may be similarly applied to the first embodiment.

In addition, in the above-mentioned embodiments, the case in which the cutting blade movement mechanism part 15 moves the cutting blade 3 along the virtual plane H has been described. However, the base section 2 may be moved to cut the embedding block B.

In addition, in the above-mentioned embodiments, the case in which the movement mechanism part 12 is not included in the height change part 51 has been described. However, the height change part 51 including the movement mechanism part 12 may be used as the height change part. In addition, the case in which the swing mechanism part 11 is not included in the inclination angle change part 52 has been described. However, the inclination angle change part 52 including the swing mechanism part 11 may be used as the inclination angle change part.

In addition, in the first embodiment, the aspect in which the boundary line between the cutting surface and the non-cutting surface of the paraffin P is used when the embedding block B is roughly cut has been described. However, when the embedding block B is not roughly cut, the boundary line between the cutting surface and the non-cutting surface of the paraffin P may be used. In this case, the thin-slice manufacturing device 1 may perform the surface matching process so that the surface of the embedding block B and the virtual plane H are parallel to each other.

In addition, in the second embodiment, the thin-slice manufacturing device 1 may estimate the inclination information of the biological sample S using the boundary line between the cutting surface and the non-cutting surface of the biological sample S when the embedding block B is roughly cut, and may perform the surface matching process so that the surface of the biological sample S and the virtual plane H are parallel to each other.

In addition, in the above-mentioned embodiments, the aspect in which the thin-slice manufacturing device 1 performs the surface matching (the surface matching process) of the cutting surface without the necessity of position detection of the embedding block B by the sensor has been described. However, the thin-slice manufacturing device 1 may include a sensor configured to detect a cutting position of the embedding block B, and may be combined with the surface matching (the surface matching process) of the cutting surface without the necessity of the position detection by the sensor to be performed.

The thin-slice manufacturing device 1 has a computer system installed therein. Then, the surface matching process and thin slice manufacturing process are stored on a computer-readable recording medium in a program type, the program is read by the computer and performed, and thus, the processes is performed. Here, the computer-readable recording medium is a magnetic disk, an opto-magnetic disk, a CD-ROM, a DVD-ROM, a semiconductor memory, or the like. In addition, the computer program is transmitted to the computer by a communication line, and the computer that receives the transmission may perform the program.

REFERENCE SIGNS LIST

1: thin-slice manufacturing device, 2: base section, 3: cutting blade, 4: vertical illumination part, 5, 5a: control unit, 10: support frame, 11: swing mechanism part, 11a: Y-axis swing mechanism part, 11b: X-axis swing mechanism part, 12: movement mechanism part, 13: block holder, 15: cutting blade movement mechanism part, 20: LED, 21: surface light source, 22: half mirror, 30: imaging part, 31: input part, 32: display part, 51: height change part, 52: inclination angle change part, 53: normal vector calculation part, 54: inclination estimation part, 55: inclination compensation part, 56: compensation designation information acquisition part, L1: optical axis, H: virtual plane, B: embedding block, S: organism sample, P: paraffin, K: cassette

What is claimed is:

1. A thin-slice manufacturing device for cutting an embedding block in which a sample is embedded by an embedding agent by using a cutting blade relatively moved with respect to the embedding block along a virtual plane to cut out thin slices, the thin-slice manufacturing device comprising:
   a radiation part configured to radiate light to the embedding block; and
   an estimation part configured to detect a boundary line between a cutting surface and a non-cutting surface formed by cutting the embedding block along the virtual plane based on reflection of light generated by the light radiated to the embedding block from the radiation part, and configured to estimate inclination information regarding an inclination of the embedding block based on the detected boundary line,
   wherein the inclination information comprises a direction of the inclination of the embedding block and a degree of inclination of the embedding block,
   the estimation part estimates the direction of the inclination based on a normal vector of the boundary line, and simultaneously, estimates the degree of inclination based on a movement amount of the boundary line and a predetermined amount when the virtual plane is moved by the predetermined amount in a direction perpendicular to the virtual plane in order to cut the embedding block,
   the radiation part switches and radiates vertical illumination light and diffuse light to the embedding block,
   the estimation part detects the boundary line based on reflection of the vertical illumination light,
   the normal vector of the boundary line is a vector in a normal direction of the boundary line in which a magnitude thereof is set as a length until to an outline of a sample obtained based on radiation of the diffuse light, and
   the estimation part estimates the direction of the inclination based on the vector in the normal direction of the boundary line in which the magnitude thereof is set as the length until to the outline of the sample.

2. The thin-slice manufacturing device according to claim 1,
   wherein the movement amount of the boundary line is a movement amount in a direction of the normal vector.

3. The thin-slice manufacturing device according to claim 1,
   wherein the normal vector of the boundary line is an average normal vector, and
   the estimation part estimates the direction of the inclination based on the average normal vector.

4. The thin-slice manufacturing device according to claim 1,
   wherein the normal vector of the boundary line is a vector having a largest magnitude among a vector in a normal direction of the boundary line having the movement amount of the boundary line as a magnitude, and
   the estimation part estimates the direction of the inclination based on the vector having the largest magnitude.

5. The thin-slice manufacturing device according to claim 1,
   wherein the estimation part estimates the direction of the inclination based on the vector having a largest magnitude among the vector in the normal direction of the boundary line in which a magnitude thereof is set as the length until to the outline of the sample.

6. The thin-slice manufacturing device according to claim 1,
   wherein the estimation part estimates the direction of the inclination based on an average vector in the normal direction of the boundary line in which a magnitude thereof is set as the length until to the outline of the sample.

7. The thin-slice manufacturing device according to claim 1, further comprising:
   a compensation part configured to compensate the inclination of the embedding block so that a predetermined cross section of the embedding block and the virtual plane are parallel to each other based on the inclination information estimated by the estimation part.

8. The thin-slice manufacturing device according to claim 7,
wherein the boundary line comprises a boundary line between a cutting surface and a non-cutting surface of the embedding agent,
the predetermined cross section of the embedding block comprises a roughly cut surface showing a predetermined cutting surface on which a rough cutting, which previously cuts a surface of the predetermined cross section of the embedding block to the predetermined cutting surface, is performed, and
the compensation part compensates the inclination of the embedding block so that the roughly cut surface and the virtual plane are parallel to each other based on the inclination information.

9. The thin-slice manufacturing device according to claim 7,
wherein the boundary line comprises a boundary line between a cutting surface and a non-cutting surface of the sample,
the predetermined cross section of the embedding block comprises a predetermined cross section of the sample, and
the compensation part compensates the inclination of the embedding block so that the predetermined cross section of the sample and the virtual plane are parallel to each other based on the inclination information.

10. The thin-slice manufacturing device according to claim 8,
wherein the boundary line comprises a boundary line between a cutting surface and a non-cutting surface of the sample,
the predetermined cross section of the embedding block comprises a predetermined cross section of the sample, and
the compensation part compensates the inclination of the embedding block so that the roughly cut surface and the virtual plane are parallel to each other based on the inclination information when the rough cutting is performed on the embedding block, and
compensates the inclination of the embedding block so that the predetermined cross section of the sample and the virtual plane are parallel to each other based on the inclination information when the rough cutting is not performed on the embedding block.

11. The thin-slice manufacturing device according to claim 7, comprising:
an inclination angle change part configured to change an inclination of a support section configured to fix the embedding block; and
an imaging part configured to image an image of the embedding block by reflection of the light in a state in which the light is radiated from the radiation part,
wherein the estimation part detects the boundary line based on the image imaged by the imaging part and estimates the inclination information based on the detected boundary line, and
the compensation part changes the inclination of the support section using the inclination angle change part based on the inclination information.

12. A thin-slice manufacturing method of cutting an embedding block in which a sample is embedded by an embedding agent by using a cutting blade relatively moving with respect to the embedding block along a virtual plane in order to cut out thin slices, the thin-slice manufacturing method comprising:
a radiation step of radiating light to the embedding block by a radiation part; and
an estimation step of detecting a boundary line between a cutting surface cut along the virtual plane and a non-cutting surface based on reflection of light generated by the light radiated to the embedding block in the radiation step by an estimation part, and estimating inclination information regarding inclination of the embedding block based on the detected boundary line,
wherein the inclination information comprises a direction of the inclination of the embedding block and a degree of inclination of the embedding block,
in the estimation step, the estimation part estimates the direction of the inclination based on a normal vector of the boundary line, and simultaneously, estimates the degree of inclination based on a movement amount of the boundary line and a predetermined amount when the virtual plane is moved by the predetermined amount in a direction perpendicular to the virtual plane in order to cut the embedding block,
in the radiation step, the radiation part switches and radiates vertical illumination light and diffuse light to the embedding block,
in the estimation step, the estimation part detects the boundary line based on reflection of the vertical illumination light,
the normal vector of the boundary line is a vector in a normal direction of the boundary line in which a magnitude thereof is set as a length until to an outline of a sample obtained based on radiation of the diffuse light, and
in the estimation step, the estimation part estimates the direction of the inclination based on the vector in the normal direction of the boundary line in which the magnitude thereof is set as the length until to the outline of the sample.

* * * * *